United States Patent
Lee et al.

(10) Patent No.: US 12,169,196 B2
(45) Date of Patent: Dec. 17, 2024

(54) HUMAN iPSC-BASED DRUG TESTING PLATFORM FOR MUSCULAR DYSTROPHY

(71) Applicant: The Johns Hopkins University, Baltimore, MD (US)

(72) Inventors: Gabsang Lee, Baltimore, MD (US); Kathryn Wagner, Baltimore, MD (US); Congshan Sun, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 966 days.

(21) Appl. No.: 16/840,302

(22) Filed: Apr. 3, 2020

(65) Prior Publication Data

US 2020/0355674 A1 Nov. 12, 2020

Related U.S. Application Data

(60) Provisional application No. 62/828,991, filed on Apr. 3, 2019.

(51) Int. Cl.
*G01N 33/50* (2006.01)
*C12N 5/074* (2010.01)
*C12N 5/077* (2010.01)

(52) U.S. Cl.
CPC ....... *G01N 33/5061* (2013.01); *C12N 5/0658* (2013.01); *C12N 5/0696* (2013.01); *C12N 2501/60* (2013.01); *C12N 2501/602* (2013.01); *C12N 2501/604* (2013.01); *C12N 2501/606* (2013.01); *C12N 2503/02* (2013.01); *C12N 2506/1307* (2013.01); *C12N 2506/45* (2013.01)

(58) Field of Classification Search
CPC ....... G01N 33/5061; G01N 2800/2878; G01N 33/5073; C12N 5/0658; C12N 5/0696; C12N 2501/60; C12N 2501/602; C12N 2501/604; C12N 2501/606; C12N 2503/02; C12N 2506/1307; C12N 2506/45
See application file for complete search history.

(56) References Cited

U.S. PATENT DOCUMENTS

| | | | | |
|---|---|---|---|---|
| 2015/0285789 | A1* | 10/2015 | Montano | G01N 33/5073 506/10 |
| 2018/0263995 | A1* | 9/2018 | Schmidt | A61K 35/34 |
| 2019/0161733 | A1* | 5/2019 | Pijnappel | C12N 5/0659 |
| 2021/0171911 | A1* | 6/2021 | Perlingeiro | G01N 33/5061 |

FOREIGN PATENT DOCUMENTS

WO WO-2017100498 A1 * 6/2017 ............. A61K 35/34

OTHER PUBLICATIONS

Sharma et al. "Myosin Heavy Chain-embryonic is a crucial regulator of skeletal muscle development and differentiation." BioRxiv (2018): 261685 (Year: 2018).*
Ishikawa et al. "Morphology-based analysis of myoblasts for prediction of myotube formation." SLAS Discov. Jan. 2019;24(1):47-56. (Year: 2019).*
Madden et al. "Bioengineered human myobundles mimic clinical responses of skeletal muscle to drugs." Elife. Jan. 9, 2015;4:e04885. (Year: 2015).*
Franzi et al. "Type 1 Interferons Inhibit Myotube Formation Independently of Upregulation of Interferon-Stimulated Gene 15." PLoS One. 2013; 8(6): e65362. (Year: 2013).*
Shelton et al. (Robust generation and expansion of skeletal muscle progenitors and myocytes from human pluripotent stem cells.) Methods .May 15, 2016;101:73-84. (Year: 2016).*

* cited by examiner

*Primary Examiner* — Titilayo Moloye
(74) *Attorney, Agent, or Firm* — Fox Rothschild LLP

(57) ABSTRACT

Methods for identifying compounds in the treatment of muscular dystrophies, include the use of disease relevant cells derived from a patient. Compounds identified by these methods are useful in the treatment of muscular dystrophy.

13 Claims, 16 Drawing Sheets
(14 of 16 Drawing Sheet(s) Filed in Color)
Specification includes a Sequence Listing.

A

| Ingenuity Canonical Pathways | z-score |
|---|---|
| Ginsenoside Rd Treated | |
| FLT3 Signaling | 2.236 |
| Role of CHK Proteins in Cell Cycle Checkpoint Control | 2 |
| Role of IL-17F in Allergic Inflammatory Airway Diseases | 2 |
| cAMP-mediated signaling | 1.604 |
| Protein Kinase A Signaling | 1.606 |
| ERK/MAPK Signaling | 1.508 |
| Fenofibrate treated | |
| TGF-β Signaling | -2.449 |
| Nitric Oxide Signaling in the Cardiovascular System | 2.121 |
| AMPK Signaling | 1.414 |
| cAMP-mediated signaling | 1.342 |

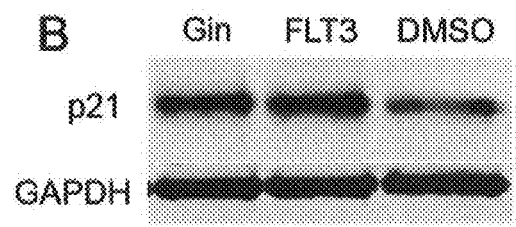

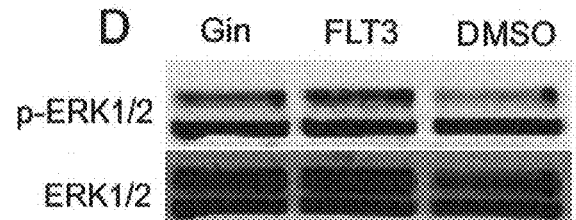

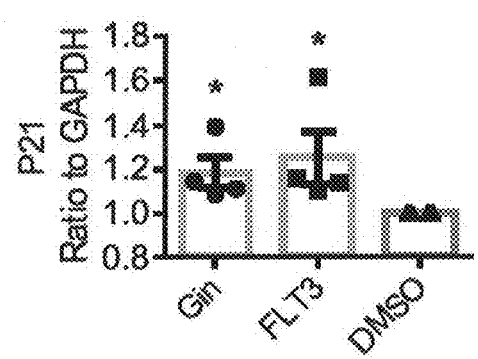

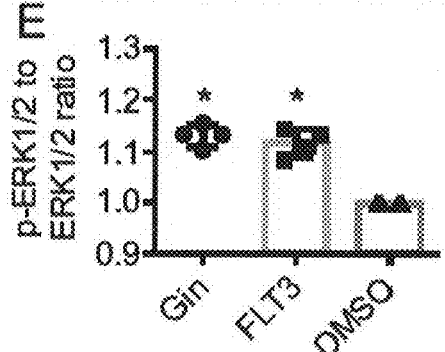

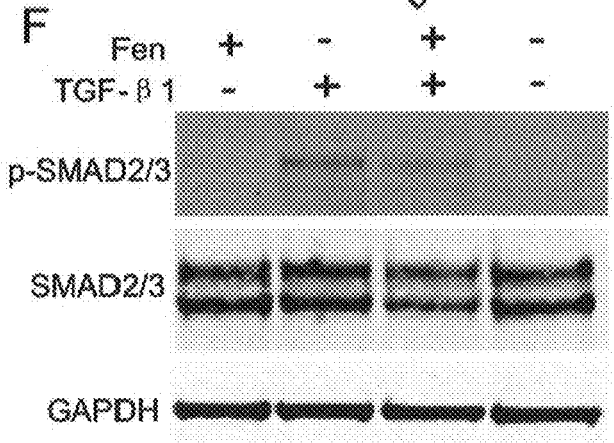

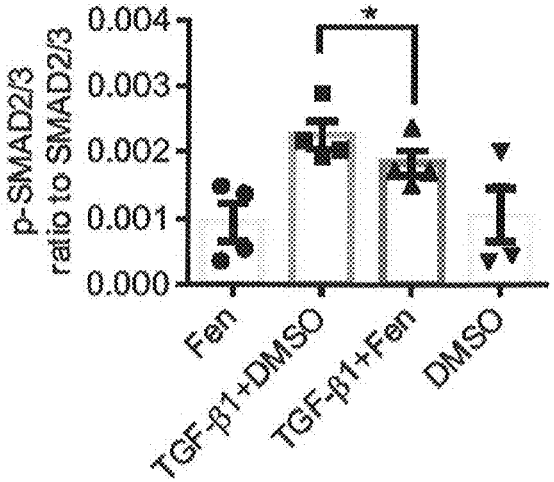

FIGS. 3A-3G

HUMAN iPSC-BASED DRUG TESTING PLATFORM FOR MUSCULAR DYSTROPHY

CROSS REFERENCE TO RELATED APPLICATIONS

This application claims the benefit of priority under 35 U.S.C. § 119(e) to U.S. Provisional Application No. 62/828,991 filed Apr. 3, 2019. The entire contents of this application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 30, 2020, is named 048317-564001US_SL.txt and is 20,135 bytes in size.

STATEMENT REGARDING FEDERALLY SPONSORED RESEARCH

This invention was made with government support under grant numbers R01NS093213 and R01AR070751 awarded by the National Institutes of Health. The government has certain rights in this invention.

FIELD OF THE INVENTION

Embodiments of the invention are directed to induced pluripotent stem cells (iPSC) and screening assays for candidate therapeutic agents.

BACKGROUND

Duchenne muscular dystrophy (DMD) is an X-chromosome linked disease that affects 1 in 5000 boys worldwide (Ryder S, et al. (2017) *Orphanet Journal of Rare Diseases* 12(1):79.1). The disease is caused by mutation in the gene encoding for dystrophin which, along with a glycoprotein complex, connects the intracellular cytoskeleton to the extracellular matrix (Angelini C (2007) *Muscle & Nerve* 36(4):424-435; Koenig M, Monaco A P, & Kunkel L M (1988) The complete sequence of dystrophin predicts a rod-shaped cytoskeletal protein. *Cell* 53(2):219-228; Hoffman E P, Monaco A P, Feener C C, & Kunkel L M (1987) Conservation of the Duchenne muscular dystrophy gene in mice and humans. *Science* 238(4825):347-350). Boys who are born with this disease suffer from loss of ambulation in early teenage years and die in early adulthood. To this day, treatment options for DMD patients are very limited. Glucocorticosteroids therapy has been the main treatment for almost three decades and is associated with a host of side effects (Angelini C & Peterle E (2012) Old and new therapeutic developments in steroid treatment in Duchenne muscular dystrophy. *Actamyologica: myopathies and cardiomyopathies: official journal of the Mediterranean Society of Myology* 31(1):9-15). Exon skipping therapy with eteplirsen targets a limited population of DMD patients and its efficacy remains controversial (Aartsma-Rus A & Krieg A M (2017) FDA Approves Eteplirsen for Duchenne Muscular Dystrophy: The Next Chapter in the Eteplirsen Saga. *Nucleic acid therapeutics* 27(1):1-3; Finkel R S, et al. (2013) *PloS one* 8(12):e81302). Meanwhile, gene therapy with adeno-associated virus (AAV) and mini-dystrophin transgene has entered clinical trials. However preexisting immunity to AAV may hinder its availability to large numbers of DMD boys (Chamberlain J R & Chamberlain J S (2017) Progress toward Gene Therapy for Duchenne Muscular Dystrophy. *Molecular therapy: the Journal of the American Society of Gene Therapy* 25(5):1125-1131; Meregalli M, et al. (2013) Perspectives of stem cell therapy in Duchenne muscular dystrophy. *The FEBS journal* 280(17):4251-4262). Even in the best-case scenario, gene therapy promises to convert a Duchenne phenotype to a milder allelic form of muscular dystrophy, Becker phenotype.

SUMMARY

There is an urgent need to search for alternative treatment options for muscular dystrophies. Accordingly, embodiments of the invention are directed, in part, to an efficient drug screening platform.

In certain embodiments, a method of screening for candidate therapeutic agents, comprises obtaining fibroblasts from a subject and generating induced pluripotent stem cells (iPSCs); differentiating the iPSCs to generate myoblasts; contacting the myoblasts with a candidate therapeutic agent; culturing the myoblasts with a detectably labeled anti-myosin heavy chain antibody; and, imaging and analyzing the myoblasts generated from the subject's iPSCs as compared to myoblasts generated from a healthy subject's iPSCs. In these and other aspects, the detectable label comprises: an immunofluorescent agent, radio labeled molecules fluorophores, radiochemical, luminescent compounds, chemoluminiscent electron-dense reagents, enzymes, biotin, radioactive compounds, non-radioactive compounds or digoxigenin. In certain embodiments, the detectable label is an immunofluorescent agent. In certain embodiments, the analysis comprises measuring average length of cells, expression of myosin heavy chain (MyHC) polypeptides as compared to positive and negative controls. In these and other aspects, the average length of cells is determined by: cell average length+0.3*MyHC (myosin heavy chain). In these and other aspects, the expression of myosin heavy chain is detected by intensity of immunofluorescent staining of MyHC polypeptides. In these and other aspects, the absolute values of cell average length are measured to include compounds which normalize myotube formation but do not increase MyHC immunofluorescence. In these and other aspects, the candidate therapeutic agents have an equal or higher value than an average value of the positive control as measured by cell average length+0.3*MyHC and intensity of MyHC staining. In these and other aspects, a candidate therapeutic agent enhances myogenic fusion abilities of patient specific myoblasts as compared to a control.

In certain embodiments, the method further comprises measuring dose responses to a candidate therapeutic agent as determined by anti-MyHC immunocytochemistry, anti-α-actinin immunocytochemistry and average cell length. In these and other aspects, the fibroblasts are reprogrammed with one or more reprograming factors to produce an iPSC. In certain embodiments, the iPSCs are cultured as single cells on defined extracellular matrix material in serum-free media. In certain embodiments, the iPSCs are cultured in medium comprising a Wnt agonist and Notch antagonist to generate myoblasts. In these and other aspects, the myoblasts are identified by an expression profile as neural cell adhesion molecule positive and human natural killer-1 negative (NCAM+/HNK1−). In certain embodiments, the subject is suffering from a muscular dystrophy. In certain embodiments, the muscular dystrophy comprises: Duchenne muscular dystrophy (DMD), Becker muscular dystrophy, congenital muscular dystrophy, myotonic dystrophy, facioscapulohumeral muscular dystrophy (FSHD), limb-girdle muscular dystrophy, oculopharyngeal muscular dystrophy, Ddstal muscular dystrophy or Emery-Dreifuss muscular dystrophy. In certain embodiments, the muscular dystrophy is Duchenne muscular dystrophy (DMD).

In certain embodiments, a myoblast is derived from an induced pluripotent stem cell (iPSC), wherein the iPSC is derived from a fibroblast from a subject with a muscular dystrophy. In certain embodiments, the muscular dystrophy comprises: Duchenne muscular dystrophy (DMD), Becker muscular dystrophy, congenital muscular dystrophy, myotonic dystrophy, facioscapulohumeral muscular dystrophy (FSHD), limb-girdle muscular dystrophy, oculopharyngeal muscular dystrophy, Ddstal muscular dystrophy or Emery-Dreifuss muscular dystrophy. In certain embodiments, the myoblast is derived from an induced pluripotent stem cell (iPSC), wherein the iPSC is derived from a fibroblast from a subject with a Duchenne muscular dystrophy (DMD).

In certain embodiments, a composition comprises a myoblast derived from an induced pluripotent stem cell (iPSC), wherein the iPSC is derived from a fibroblast from a subject with a muscular dystrophy. In certain embodiments, the muscular dystrophy comprises: Duchenne muscular dystrophy (DMD), Becker muscular dystrophy, congenital muscular dystrophy, myotonic dystrophy, facioscapulohumeral muscular dystrophy (FSHD), limb-girdle muscular dystrophy, oculopharyngeal muscular dystrophy, Ddstal muscular dystrophy or Emery-Dreifuss muscular dystrophy. In certain embodiments, the muscular dystrophy is Duchenne muscular dystrophy (DMD).

In certain embodiments, a method of producing an induced pluripotent stem cell (iPSC), comprises obtaining a biological sample comprising fibroblasts or obtaining fibroblasts from a subject with a muscular dystrophy, and reprograming the fibroblasts with one or more reprograming factors to produce an iPSC. In these and other aspects, the iPSCs are cultured as single cells on defined extracellular matrix material in serum-free media. In certain embodiments, the one or more reprograming factors comprise: Oct-3/4, paired box gene family (PAX), Sox family, Klf family, Myc family, Glis1, Nanog, LIN28 or combinations thereof. In these and other aspects, the Sox family comprises Sox1, Sox2, Sox3, Sox15, Sox 18 or combinations thereof. In certain embodiments, the Klf family comprises Klf1, Klf2, Klf4, Klf5 or combinations thereof. In certain embodiments, the Myc family comprises c-myc, L-myc, N-myc or combinations thereof. In certain embodiments, the PAX gene is PAX3.

In certain embodiments, method of producing a myoblast, comprises obtaining a biological sample comprising fibroblasts or obtaining fibroblasts from a subject with a muscular dystrophy, e.g. Duchenne muscular dystrophy (DMD), and reprograming the fibroblasts with one or more reprograming factors to produce an iPSC, and culturing the iPSCs in medium comprising a Wnt agonist and a Notch antagonist to generate myoblasts. In certain embodiments, the myoblasts are identified by an expression profile as neural cell adhesion molecule positive and human natural killer-1 negative (NCAM$^+$/HNK1$^-$).

In certain embodiments, a Wnt agonist comprises 5-(Phenylsulfonyl)-N-4-piperidinyl-2-(trifluoromethyl)benzene sulfonamide hydrochloride (WAY-316606), 2-Amino-4-[3,4-(methylenedioxy)benzylamino]-6-(3-methoxyphenyl)pyrimidine (BML-284), (hetero)arylpyrimidines, 2-[2-(4-Acetylphenyl)diazenyl]-2-(3,4-dihydro-3,3-dimethyl-1(2H)-isoquinolinylidene)acetamide (IQ1), (2S)-2-[2-(Indan-5-yloxy)-9-(1,1'-biphenyl-4-ylmethyl)-9H-purin-6-ylamino]-3-phenyl-propan-1-ol (QS11), N-[2-(3,4-dimethoxyphenyl)ethyl]-2-ethyl-5-(phenylsulfonul) benzenesulfonamide, (1-(4-(Naphthalen-2-yl)pyrimidin-2-yl)piperidin-4-yl)methanamine, 3-(2,4-Dichlorophenyl)-4-(1-methyl-1H-indol-3-yl)-1H-pyrrole-2,5-dione, 2-amino-4-[3,4-(methylenedioxy)benzyl-amino]-6-(3-methoxyphenyl)pyrimidine, Dichlorophenyl)-4-(1-methyl-1H-indol-3-yl)-1H-pyrrole-2,5-dione (SB-216763), 6-[[2-[[4-(2,4-Dichlorophenyl)-5-(5-methyl-1H-imidazol-2-yl)-2-pyrimidinyl]amino]ethyl]amino]-3-pyridinecarbonitrile (CHIR99021), (2'Z,3'E)-6-Bromoindirubin-3'-oxime (BIO), 3-[9-Fluoro-2-(piperidin-1-ylcarbonyl)-1,2,3,4-tetrahydro[1,4]diazepino[6,7,1-hi]indol-7-yl]-4-imidazo[1,2-a]pyridin-3-yl-1H-pyrrole-2,5-dione (LY2090314), dichloroacetic acid (DCA) or combinations thereof.

In certain embodiments, a Notch antagonist comprises gamma-secretase inhibitors (GSIs), alpha-secretase inhibitors (ASIs), N—[N-(3,5-Difluorophenylacetyl-L-alanyl)]-5-phenylglycine t-Butyl ester (DAFT), (5S)-(tert-Butoxycarbonylamino)-6-phenyl-(4R)-hydroxy-(2R)-benzylhexanoyl)-L-leucy-L-phenylalaninamide (GSI L685,458), (s,s)-2-(3,5-Difluorophenyl)-acetylamino]-N-(1-methyl-2-oxo-5-phenyl-2,3-dihydro-1H-benzo[e][1,4]diazepin-3-yl)-propionamide (compound E), dibenzazepine compounds, 7-amino-4-chloro-3-methoxyisocoumarin (JLK6), [11-endo]-N-(5,6,7,8,9,10-hexahydro-6,9-methano benzo[9][8]annulen-11-yl)-thiophene-2-sulfonamide (Compound 18), stapled peptides, peptides, peptidomimetics, antibodies, antibody fragments, enzymes, small molecules or combinations thereof.

In certain embodiments, a method of treating Duchenne muscular dystrophy (DMD) comprising administering a therapeutic agent to a subject a pharmaceutical composition comprising a therapeutically effective amount of a therapeutic agent identified by the methods embodied herein. In certain embodiments, the therapeutic agent comprises a therapeutically effective amount of ginsenoside Rd, fenofibrate or a combination thereof.

Exemplary effective doses of the ginsenoside Rd, fenofibrate or a combination thereof include between 0.1 μg/kg and 100 mg/kg body weight, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900 μg/kg body weight or 1, 2, 3, 4, 5, 6, 7, 8, 9, 10, 20, 30, 40, 50, 60, 70, 80, 90, or 100 mg/kg body weight.

In some cases, the ginsenoside Rd, fenofibrate, a candidate therapeutic agent(s) or combinations thereof, is administered daily, e.g., every 24 hours. Or, the ginsenoside Rd, fenofibrate, a candidate therapeutic agent(s) or combinations thereof, is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours. Exemplary effective daily doses of the ginsenoside Rd, fenofibrate, a candidate therapeutic agent(s) or combinations thereof, include between 0.1 μg/kg and 100 μg/kg body weight, e.g., 0.1, 0.3, 0.5, 1, 5, 10, 15, 20, 25, 30, 35, 40, 45, 50, 55, 60, 65, 70, 75, 80, 85, 90, 95, or 99 μg/kg body weight.

Alternatively, the ginsenoside Rd, fenofibrate, a candidate therapeutic agent(s) or combinations thereof, is administered about once per week, e.g., about once every 7 days. Or, the ginsenoside Rd, fenofibrate, a candidate therapeutic agent(s) or combinations thereof, is administered twice per week, three times per week, four times per week, five times per week, six times per week, or seven times per week. Exemplary effective weekly doses of the ginsenoside Rd, fenofibrate, a candidate therapeutic agent(s) or combinations thereof, include between 0.0001 mg/kg and 4 mg/kg body weight, e.g., 0.001, 0.003, 0.005, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, or 4 mg/kg body weight. For example, an effective weekly dose of the ginsenoside Rd, fenofibrate, a candidate therapeutic agent(s) or combinations thereof, is between 0.1 µg/kg body weight and 400 µg/kg body weight.

In some cases, subjects receive two 6-week cycles consisting of 4 weekly ginsenoside Rd, fenofibrate, a candidate therapeutic agent(s) or combinations thereof, intravenous doses followed by a 2-week rest period. Ultimately, the attending physician or veterinarian decides the appropriate amount and dosage regimen.

In certain embodiments, the invention relates to methods for treating a patient with Duchenne muscular dystrophy (DMD), comprising intravenously administering to the patient one or more compounds identified by the screening assays embodied herein, e.g. ginsenoside Rd, fenofibrate, at a therapeutically effective dose once, twice, three times etc., weekly for more than 168 weeks, such that disease progression in the patient is delayed as measured by the 6 Minute Walk Test (6MWT), thereby treating the patient. In certain embodiments, the candidate therapeutic agents maintain ambulation, or reduce the loss of ambulation, in a patient with Duchenne muscular dystrophy (DMD) or other muscular dystrophies, comprising intravenously administering to the patient a once weekly dose for more than 168 weeks, thereby maintaining ambulation, or reducing the loss of ambulation relative to baseline, in the patient as measured by the 6 Minute Walk Test (6MWT). In certain embodiments, the patient maintains ambulation relative to baseline or loses 50% or less (e.g., 49, 48, 47, 46, 45, 44, or 43% or less) ambulation, relative to baseline, by 192 weeks as measured by the 6 Minute Walk Test (6MWT).

In certain embodiments, one or more candidate therapeutic agents are administered, e.g. intravenously, to the patient one or more candidate therapeutic agents at a therapeutically effective dose at least once per week for more than 192 weeks (e.g., 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 255, or 260 or more), such that disease progression in the patient is delayed as measured by the 6 Minute Walk Test (6MWT), thereby treating the patient.

In another aspect, the invention candidate therapeutic agents maintain pulmonary function or reduce loss of pulmonary function in a patient with Duchenne muscular dystrophy (DMD) or other muscular dystrophies. In these and other aspects of the invention, pulmonary function is measured as Maximum Expiratory Pressure (MEP). In other aspects of the invention, pulmonary function is measured as Maximum Inspiratory Pressure (MIP). In yet other aspects of the invention, pulmonary function is measured as Forced Vital Capacity (FVC).

In certain embodiments, the patient is administered one or more candidate therapeutic agents as identified by the methods embodied herein in combination with one or more other therapies, e.g. steroids. In any of the foregoing and other aspects of the invention, the patient is administered a corticosteroid (e.g., prednisone) in addition to administration of one or more candidate therapeutic agents. A corticosteroid can be administered prior to treatment with the candidate therapeutic agents or in conjunction with candidate therapeutic agent treatment or subsequent to treatment with any one or more candidate therapeutic agents. In some embodiments, any of the methods described herein comprise administering to the patient a steroid, e.g., a corticosteroid. In some embodiments, the corticosteroid is Betamethasone, Budesonide, Cortisone, Dexamethasone, Hydrocortisone, Methylprednisolone, Prednisolone, Prednisone, or deflazacort. In some embodiments of any of the methods described herein, the patient is on background steroids (e.g., intermittent or continuous/chronic background steroid therapy).

In these and other aspects of the invention, ambulation is maintained for at least 216 weeks of treatment.

In certain embodiments, the patient's loss of ambulation between about three years of treatment and about four years of treatment is no greater than 20%. In other aspects of the invention, the patient's loss of ambulation between about three years of treatment and about four years of treatment is no greater than 30%. In yet other aspects of the invention, the patient's loss of ambulation between about three years of treatment and about four years of treatment is no greater than 40%. In other aspects of the invention, the patient's loss of ambulation between about three years of treatment and about four years of treatment is no greater than 50%.

In certain embodiments, the patient's loss of ambulation is no greater than about 20% relative to base line. In other aspects of the invention, the patient's loss of ambulation is no greater than about 30% relative to base line. In yet others aspects of the invention, the patient's loss of ambulation is no greater than about 40% relative to base line. In other aspects of the invention, the patient's loss of ambulation is no greater than about 50% relative to base line. In other aspects of the invention, the patient's loss of ambulation is no greater than about 60% relative to base line.

In certain embodiments, the patient maintains a 6 Minute Walk Distance (6MWD) of at least 55 meters at 216 weeks of treatment. In other aspects of the invention, the patient maintains a 6 Minute Walk Distance (6MWD) of at least 100 meters at 216 weeks of treatment. In yet other aspects of the invention, the patient maintains a 6 Minute Walk Distance (6MWD) of at least 200 meters at 216 weeks of treatment. In other aspects of the invention, the patient maintains a 6 Minute Walk Distance (6MWD) of at least 300 meters at 216 weeks of treatment. In another aspects of the invention, the patient maintains a 6 Minute Walk Distance (6MWD) of at least 400 meters at 216 weeks of treatment.

In certain embodiments, a method of diagnosing or monitoring disease progression in subjects, comprises: obtaining fibroblasts from a subject and generating induced pluripotent stem cells (iPSCs); differentiating the iPSCs to generate myoblasts; culturing the myoblasts with a detectably labeled anti-myosin heavy chain antibody; and, imaging and analyzing the myoblasts generated from the subject's iPSCs as compared to myoblasts generated from a healthy subject's iPSCs; thereby, diagnosing or monitoring disease progression in a subject. In this and other aspects of the invention, the subject is at risk of or suffering from a muscular dystrophy. In these and other aspects of the invention, the muscular dystrophy comprises: Duchenne muscular dystrophy (DMD), Becker muscular dystrophy, congenital muscular dystrophy, myotonic dystrophy, facioscapulohumeral muscular dystrophy (FSHD), limb-girdle muscular dystrophy, oculopharyngeal muscular dystrophy, distal muscular dystrophy or Emery-Dreifuss muscular dystrophy. In these and other aspects of the invention, the muscular dystrophy is Duchenne muscular dystrophy (DMD). In these and other aspects of the invention, in vitro fusion rates of patient hiPSC-derived myoblasts are decreased as compared to a healthy subject. In these and other aspects of the invention, in vitro fusion rates of patient hiPSC-derived myoblasts are decreased the disease progresses as compared to a healthy subject and as compared to the patient's results measured over time.

Other aspects are described infra.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used in this specification and the appended claims, the term "or" is generally employed in its sense including "and/or" unless the content clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

The term "agent" is used to describe a compound that has or may have a therapeutic or pharmacological activity. Agents include compounds that are known drugs, compounds for which therapeutic activity has been identified but which are undergoing further therapeutic evaluation, and compounds that are members of collections and libraries that are to be screened for a pharmacological activity.

The term "antagonist" is used in the broadest sense, and includes any molecule that partially or fully blocks, inhibits, or neutralizes a biological activity of a native molecule disclosed herein, e.g. Notch or molecules associated in the signaling pathways thereof. In a similar manner, the term "agonist" is used in the broadest sense and includes any molecule that mimics a biological activity of a native molecule disclosed herein, e.g. Wnt or molecules associated in the signaling pathways thereof. Suitable agonist or antagonist molecules specifically include agonist or antagonist antibodies or antibody fragments, fragments or amino acid sequence variants of native polypeptides, peptides, peptidomimetics, antisense oligonucleotides, small organic molecules, small molecules, carbohydrates, etc. Methods for identifying agonists or antagonists of a desired molecule may comprise contacting the molecule with a candidate agonist or antagonist molecule and measuring a detectable change in one or more biological activities normally associated with the molecule.

As used herein, "biological samples" include solid and body fluid samples. The biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils, thymus and skin, or samples taken from tumors. Examples of "body fluid samples" include, but are not limited to blood, serum, semen, prostate fluid, seminal fluid, urine, feces, saliva, sputum, mucus, bone marrow, lymph, and tears.

The term "chemiluminescent compound" includes any compound, composition or molecule capable of emitting light in response to a chemical reaction. A "bioluminescent compound" refers to a naturally occurring form of a chemiluminescent compound. Examples of chemiluminescent compounds include: lucigenin, luminol. Examples of bioluminescent compounds include: luciferins, coelenterazines. The emission from chemiluminescent compounds can be detected by luminometers or scanning spectrometers.

The term "combination therapy", as used herein, refers to those situations in which two or more different agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

Certain methodologies of the instant invention include a step that involves comparing a value, level, feature, characteristic, property, etc. to a "control", referred to interchangeably herein as an "appropriate control" or "suitable control". A "control", "suitable control" or "appropriate control" is a control or standard familiar to one of ordinary skill in the art useful for comparison purposes. In one embodiment, a "suitable control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention to a subject. In another embodiment, a "suitable control" is a value, level, feature, characteristic, property, etc. determined in a cell or organism, e.g., a control or normal cell or organism, exhibiting, for example, normal traits. In yet another embodiment, a "suitable control" or is a predefined value, level, feature, characteristic, property, etc.

A "detectable label" or a "label" is a composition detectable by spectroscopic, photochemical, biochemical, immunochemical, chemical or any other means. For example, useful labels include radio labeled molecules, fluorophores, luminescent compounds, electron-dense reagents, enzymes (e.g., as commonly used in an ELISA), biotin, digoxigenin, or haptens and proteins which can be made detectable, e.g., by incorporating a label into the peptide or used to detect antibodies specifically reactive with the peptide.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

By "enhance" or "increase" or "restore" or "stimulate," refers generally to the ability of an agent to produce or cause a greater physiological response (i.e., downstream effects) in a cell or a subject, as compared to the response caused by either no ginsenoside Rd, fenofibrate, a candidate therapeutic agent(s) or combinations thereof, or a control compound. A measurable physiological response may include increased expression of a functional form of, e.g. a dystrophin protein, or increased dystrophin-related biological activity in muscle tissue, among other responses apparent from the understanding in the art and the description herein. Increased muscle function can also be measured, including increases or improvements in muscle function by about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%. The percentage of muscle fibers that express a functional dystrophin can also be measured, including increased dystrophin expression in about 1%, 2%, %, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibers. For instance, it has been shown that around 40% of muscle function improvement can occur if 25-30% of fibers express dystrophin (see, e.g., DelloRusso et al., *Proc Natl Acad Sci USA* 99: 12979-12984, 2002).

The term "fluorophore" includes any compound, composition or molecule capable of emitting light in response to irradiation. In many instances, fluorophores emit light in the visible region of light. In other instances, the fluorophores can emit light in the non-visible regions of light, such as ultraviolet, near-ultraviolet, near-infrared, and infrared. For example and without limitation, examples of fluorophores include: quantum dots; nanoparticles; fluorescent proteins, such as green fluorescent protein and yellow fluorescent protein; heme-based proteins or derivatives thereof; carbocyanine-based chromophores, such as IRDye 800CW, Cy 3, and Cy 5; coumarin-based chromophores, such as (7-diethylamino-3-(4'-maleimidylphenyl)-4-methylcoumarin) (CPM); fluorine-based chromophores, such as fluorescein, fluorescein isothiocyanate (FITC); and numerous ALEXA FLUOR™ chromophores and ALEXA FLUOR™ bioconjugates, which absorb in the visible and near-infrared spectra. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners).

The term "high-throughput screening" or "HTS" refers to a method drawing on different technologies and disciplines, for example, optics, chemistry, biology or image analysis to permit rapid, highly parallel biological research and drug discovery. HTS methods are known in the art and they are generally performed in multiwell plates with automated liquid handling and detection equipment; however it is envisioned that the methods of the invention may be practiced on a microarray or in a microfluidic system.

As used herein, the terms "individual" and "subject" may be used interchangeably and refer to a mammal, including, but not limited to, a human or non-human mammal, such as a bovine, equine, canine, ovine, or feline. Preferably, the individual or subject is a human. Patients are also individuals or subjects herein.

An "increased" or "enhanced" amount may include, e.g., an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by the absence of an agent or a control compound.

The term "library" or "drug library" as used herein refers to a plurality of chemical molecules (test compound), a plurality of nucleic acids, a plurality of peptides, or a plurality of proteins, organic or inorganic compounds, synthetic molecules, natural molecules, or combinations thereof.

The term "luminescent component" or "luminescent compound" as used herein refers to a component capable of absorbing energy, such as electrical (e.g., electro-luminescence), chemical (e.g., chemi-luminescence) or acoustic energy and then emitting at least some fraction of that energy as light over time. The term "component" as used herein includes discrete compounds, molecules, bioluminescent proteins and macro-molecular complexes or mixtures of luminescent and non-luminescent compounds or molecules that act to cause the emission of light.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

The term "reduce" or "inhibit" relates generally to the ability of ginsenoside Rd, fenofibrate, a candidate therapeutic agent(s) or combinations thereof, to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of muscular dystrophy, or reductions in the expression of, for example, defective forms of dystrophin, such as the altered forms of dystrophin that are expressed in individuals with muscular dystrophies. A "decrease" in a response may include, e.g., a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

As used herein, the "6-Minute Walk Test" (6MWT) is a self-paced walking test that measures the distance an individual is able to walk on a hard, flat surface for 6 minutes. Originally developed for assessment of aerobic activity in patients with respiratory disease, the 6MWT is now validated in numerous other patient populations, including those with musculoskeletal diseases (e.g., Duchenne/Becker muscular dystrophy, facioscapulohumeral muscular dystrophy, spinal muscle atrophy), and has been used as an efficacy measure in clinical studies of patients with muscular and metabolic disorders. The 6MWT has also been used as an outcome measure in clinical studies of patients with other rare diseases, such as Pompe disease) Hunter syndrome, and Morquio A syndrome (McDonald, Craig et al., (2010). The 6-minute walk test in Duchenne/Becker muscular dystrophy: Longitudinal observations. Muscle & nerve. 42. 966-74. 10.1002/mus.21808).

As used herein, the term "stable disease", "stabilized", "stabilization" or like grammatical terms means a less than 20 (e.g., less than 19, 18, 17, 16, 15, 14, 13, 12, 11, 10, 9, 8, 7, 6, 5, 4, 3, 2, or 1) % increase or decrease is at least one measurable or evaluable aspect of a disease. Thus, in some embodiments, a patient with stable ambulation over a given treatment period has no greater than a 20% decrease in ambulation during that treatment period. In some embodiments, a patient with stable ambulation over a given treatment period has no greater than a 10% decline in ambulation during that treatment period. In some embodiments, a patient with stable ambulation over a given treatment period has no greater than a 5% decline in ambulation during that treatment period. In some embodiments, a patient with stable ambulation over a given treatment period has no greater than a 2.5% decline in ambulation during that treatment period. In some embodiments, a patient with stable ambulation over a given treatment period has no greater than a 1% decline in ambulation during that treatment period. For example, a patient with stable ambulation between about week 168 and about week 192 may be one who experiences an additional loss of ambulation during that period that is no greater than 5 (e.g., less than 4, 3, 2, or 1) %, relative to baseline.

A stapled peptide is a peptide that has a synthetic brace ("staple"). Peptides with multiple, tandem staples are sometimes referred to as stitched peptides. (Iegre, Jessica et al. "Stapled peptides as a new technology to investigate protein-protein interactions in human platelets" *Chemical Science* vol. 9, 20 4638-4643. 25 Apr. 2018, doi:10.1039/c8sc00284c).

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A: Flow-chart of primary compound screening showing the screening process where patient's fibroblasts were induced to hiPSCs and differentiated into myoblasts. These patient iPSC-derived myoblasts were expanded and treated with compounds from JHCCL (v1.3). Cells were fixed and stained with MyHC antibody, imaged and analyzed by BD pathway 855 automated imaging system. FIG. 1B: Graph of distinguishable algorithm 1 values between gentamicin and DMSO treated D2 myoblasts (z'=0.58). FIG. 1C: Graph of distinguishable algorithm 2 values between gentamicin and DMSO treated D2 myoblasts (z'=0.59). FIG. 1D: 9 primary hit compounds (listed) were plotted based on two parameters used in algorithms: normalized cell average length and normalized MyHC intensity.

FIG. 2A: Representative images of Saponin Q., fenofibrate, clomiphene, gentamicin and DMSO treated D2 myoblasts along with healthy hiPSC-derived myoblasts showing MyHC positive myotubes. FIG. 2B: Cell average length dose-response curve of Saponin Q., fenofibrate, clomiphene and gentamicin. FIG. 2C: Representative image of ginsenoside Rd-treated myoblasts labeled by MyHC. FIG. 2E Cell average length dose-response curve of ginsenoside Rd (FIGS. 2E-2F) Western blot quantification of MEF2C protein level post Saponin Q. and ginsenoside Rd treatment alongside healthy hiPSC derived myoblasts control and DMSO negative controls, *P 5 0.05, n=3. FIG. 2G: Quantification of MEF2C expressing nuclei of saponin Q. and ginsenoside Rd-treated D2 myoblasts, n=3, *P 5 0.05. (Data=Mean±SEM, one-way ANOVA with Dunnett's multiple comparison test with DMSO negative control).

FIGS. 3A-3G are a series of illustrations, blots and graphs showing that two selected compounds ginsenoside Rd and fenofibrate function via FLT3 signaling and TGF-β signaling, respectively. FIG. 3A: Top pathways selected by ingenuity pathway analysis of microarray result from ginsenoside Rd and fenofibrate-treated D2 myoblasts for 24 hours. Absolute z-score values above 2 were highlighted in red. FIGS. 3B and 3D: Quantification of western blot of p21 protein expression in D2 myoblasts treated with ginsenoside (25 μM), FLT3 recombinant protein (100 ng/ml) or DMSO for 30 min, n=4, *P≤0.05. FIG. 3C, 3E: Quantification of western blot of phosphorylated ERK 1/2 (p-ERK 1/2) in D2 myoblasts treated with ginsenoside (25 μM), FLT3 recombinant protein (100 ng/ml) or DMSO for 30 min, n=4, *P≤0.05. FIGS. 3F-3G: Quantification of western blot of phosphorylated SMAD2/3 (p-SMAD2/3) after the combination treatment of fenofibrate (8 μM) and/or TGF-β1 recombinant protein (40 ng/ml) for 24 h, n=4, *P≤0.05. (Data=Mean±SEM, FIGS. 3D, 3E: one-way ANOVA with Dunnett's multiple comparison test with DMSO negative control, FIG. 3G: one-way ANOVA with Tukey's multiple comparison test).

FIG. 4A: Scheme showing procedure of compound treatment of mdx mice. FIG. 4B: Body weight of mdx mice measured weekly from 3-week old to 10-week old. Sham control was mdx mice treated with standard diet, n=7 for all 3 groups. FIGS. 4C-4D: Staining and quantification of Masson's Trichrome-labeled fibrotic area (blue) in diaphragm muscle of mice, n(sham)=14, n(gin)=8, n(fen)=8, *P≤0.05, scale bar=200 μm. FIG. 4E: Measurement of fore-limb grip strength normalized to body weight from mdx mice treated with ginsenoside Rd or fenofibrate, n(sham)=16, n(gin)=8, n(fen)=9, *P≤0.05. FIG. 4F: Maximum distance mdx mice ran, n(sham)=16, n(gin)=8, n(fen)=9, **P≤0.01.

FIG. 5A: Illustration of the point mutation in dystrophin gene of D2325 patient (SEQ ID NOS: 1-3; full-length sequence disclosed as SEQ ID NO: 88 and full-length sequence with point mutation disclosed as SEQ ID NO: 89). FIG. 5A also discloses SEQ ID NOS 86-87, respectively, in order of appearance. FIG. 5B: Representative image of MyHC antibody-labeled myotubes compared with myoblasts derived from healthy hiPSC or D2 myoblasts, scale bar=50 μm. FIG. 5C: Quantification of fusion index of (FIG. 5B) n=9 for both groups, *** P≤0.001. d, Algorithm 1 plot of all tested compounds along with DMSO (blue) and gentamicin (red) treated D2 cells. (Data=Mean±SEM, student's t-test).

FIG. 7A: 9 primary hit compounds dose-response measured by MyHC antibody immunofluorescent intensity/nuclei. Concentrations of compounds were 0.001, 0.01, 0.1, 1, 2, 3, 4, 6 μM, except for saponin Q. which was 0.001, 0.01, 0.1, 0.2, 0.4, 0.6, 1 μM (n=3 for all). FIG. 7B: 9 primary hit compounds dose-response measured by α-actinin antibody immunofluorescent intensity/nuclei. Concentrations were same as in (FIG. 7A) (n=3 for all). FIGS. 7C-7E: Dose-response measured by cell average length of 3 analogs of saponin Q (n=3). FIGS. 7F-7G: Dose-response measured by cell average length of 2 analogs of fenofibrate (n=3). (Data=Mean±SEM).

FIGS. 9B and 9C: Correlation between log 2 fold change from microarray and from qPCR for ginsenoside treatment (FIG. 9B) (5 µM, 24 h) vs. DMSO (control) treatment; fenofibrate treatment (FIG. 9C) (8 µM, 24 h) vs. DMSO (control) treatment (n=3 for all groups).

FIG. 10A: Quantification of Evans blue dye-stained area signifying necrotic fibers (n(sham)=7, n(gin)=6, n(feno)=3) in gastrocnemius muscle and (FIG. 10B) Percentage of central nucleated fibers in tibialis anterior (TA) muscle (n(sham)=12, n(gin)=8, n(feno)=8) from mdx mice treated by ginsenoside Rd, fenofibrate along with the sham control. FIG. 10C: Specific force (muscle force normalized to muscle mass (MM), g/g) of TA muscle. FIG. 10D: Specific force (muscle torque normalized to muscle mass (MM), N·mm/g) generated by quadricep (Quad) muscle from mdx mice treated by ginsenoside Rd or fenofibrate along with the sham control (n=5 for all 3 groups). FIGS. 10E-10G) cholesterol (FIG. 10E), HDL (FIG. 10F) and triglycerides (FIG. 10G) content in serum from mice treated with fenofibrate and sham control (n(sham)=9, n(feno)=5, P≤0.01, *P≤0.001, ****P≤0.0001). (Data=Mean±SEM, a-d: one-way ANOVA with Dunnett's multiple comparison test with sham control, e-g: student's t-test)

DETAILED DESCRIPTION

Figures 1A, 1B, 1C:
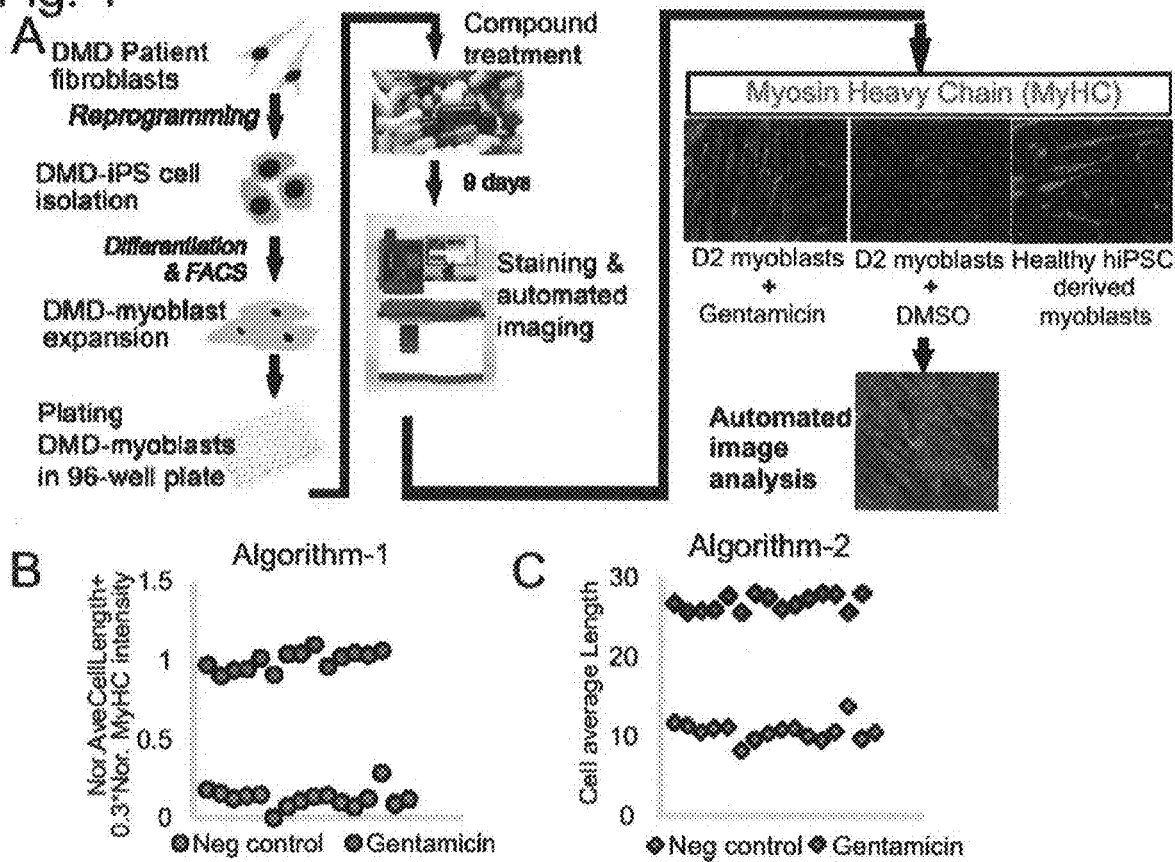
FIGS. 1A-1D are a series of flow charts, graphs and image analyses demonstrating that the primary compound screening identified 9 hit compounds.

Drug development costs a significant amount of time and resources for new pharmaceutical drugs. Progress has been limited for orphan diseases such as Duchenne muscular dystrophy (DMD). Here, an exemplary drug screening campaign is described using human induced pluripotent stem cells (hiPSCs) and the identification of two potential drugs effective in a DMD mouse model (mdx). A DMD-hiPSC screening platform utilizing high-content imaging to identify hit compounds that enhance myogenic fusion abilities of patient-specific myoblasts. Among 1524 compounds (Johns Hopkins Clinical Compound library), two hit compounds increased in vitro fusion rates of DMD patient hiPSC-derived myoblasts. Transcriptional profiling revealed that the function of two selected compounds, ginsenoside Rd (natural product, ginseng extract) and fenofibrate (FDA-approved drug), are associated with FLT3 signaling and TGF-β signaling, respectively. Preclinical tests in mdx mice show that the treatment of the two hit compounds can ameliorate the skeletal muscle phenotypes caused by dystrophin deficiency, suggesting the therapeutic potential of these two compounds. The study demonstrates the feasibility of early-stage drug development for rare and neglected diseases using symptom-relevant cells derived from patient-specific hiPSCs.

Accordingly, embodiments of the invention are directed in part to a screening process for the identification of drugs in the treatment of muscular dystrophies. In general, the steps include obtaining fibroblasts from a patient, e.g., a patient that has been diagnosed or suffering from a muscular dystrophy, such as, for example, Duchenne's muscular dystrophy (DMD). These fibroblasts are then induced to hiPSCs and differentiated into myoblasts. These patient iPSC-derived myoblasts are then expanded and treated with compounds from a compound library, for example. Cells were fixed and stained with MyHC antibody, imaged and analyzed by an automated imaging system. Primary hit compounds were plotted based on two parameters used in algorithms: normalized cell average length and normalized MyHC intensity.

Generation of Myoblasts

To harness the potential of human iPSCs, a protocol to direct hPSCs into the skeletal muscle lineage was developed by the inventors (Choi et al., 2016, *Cell Reports* 15, 2301-2312; incorporated herein in its entirety). Briefly, as the somite is an intermediate stage between hPSCs and myogenic progenitor cells a MESOGENIN1::eGFP reporter hESC line was generated with the CRISPR/Cas9 system. MESOGENIN1 is a genetic marker for the pre-somite mesoderm fate. Brief treatment (4 days after day 0 of differentiation) with CHIR99021, a GSK-3β inhibitor, significantly increased expression of MESOGENIN1::eGFP (80.8%±11.3% cells out of total cells in a dish), TBX6 (67.4%±10.4%), and PAX3 in a dose-dependent manner at day 4 and gave rise to myogenic cells expressing MyHC (MF20), MYOG, and MYOD at day 40 (30.4%±13.7%, 37.7%±5.78%, and 30.4%±13.70%, respectively). CHIR99021 appeared to activate the canonical WNT signaling pathway, confirmed by β-catenin translocation into the nucleus. WNT activation and inhibition of the PI3K pathway was sufficient for induction of MESOGENIN1::eGFP from hPSCs. To increase the speed and efficacy of myogenic specification, treatment from day 4 to day 12 with DAPT, a γ-secretase inhibitor that blocks Notch signaling, promoted a robust and fast myogenic differentiation. At day 30, 63.6%±9.68% of cells were MF20$^+$, and 61.5%±11.0% were MYOGENIN$^+$.

The resulting "CHIR99021-DAPT culture" in defined N2 media was tested on multiple hiPSC lines (>10 different clones) and consistently resulted in differentiation of myoblasts into multinucleated and spontaneously contractile myotubes. The hESC- and hiPSC-derived myotubes in CHIR99021-DAPT culture were further characterized by transmission electron microscopy. The spontaneously contracting myotubes showed a highly organized structure, including intact sarcomeres with distinct Z-lines, M-lines, and I-bands.

As discussed in the examples section which follows, the DMD-hiPSC are differentiated into myoblasts in chemically defined conditions that is free from animal feeder cells, serum or growth factors (15). This differentiation protocol involves plating single hiPSCs on defined extracellular matrix material and growing them for 25-30 days in serum-free medium with temporal activation of WNT and inhibition of NOTCH pathways.

Wnt:

The conserved Wnt/β-Catenin pathway regulates stem cell pluripotency and cell fate decisions during development. This developmental cascade integrates signals from other pathways, including retinoic acid, FGF, TGF-β, and BMP, within different cell types and tissues. The Wnt ligand is a secreted glycoprotein that binds to Frizzled receptors, leading to the formation of a larger cell surface complex with LRP5/6. Frizzleds are ubiquitinated by ZNRF3 and RNF43, whose activity is inhibited by R-spondin binding to LGR5/6. In this manner R-spondins increase sensitivity of cells to the Wnt ligand. Activation of the Wnt receptor complex triggers displacement of the multifunctional kinase GSK-3β from a regulatory APC/Axin/GSK-3β-complex. In the absence of Wnt-signal (Off-state), β-catenin, an integral E-cadherin cell-cell adhesion adaptor protein and transcriptional co-regulator, is targeted by coordinated phosphorylation by CK1 and the APC/Axin/GSK-3β-complex leading to its ubiquitination and proteasomal degradation through the β-TrCP/Skp pathway. In the presence of Wnt ligand (On-state), the co-receptor LRPS/6 is brought in complex with Wnt-bound Frizzled. This leads to activation of Dishevelled (Dvl) by sequential phosphorylation, poly-ubiquitination, and polymerization, which displaces GSK-3β from APC/Axin through an unclear mechanism that may involve substrate trapping and/or endosome sequestration. Stabilized β-catenin is translocated to the nucleus via Racl and other factors, where it binds to LEF/TCF transcription factors, displacing co-repressors and recruiting additional co-activators to Wnt target genes. Additionally, β-catenin cooperates with several other transcription factors to regulate specific targets. Importantly, researchers have found β-catenin point mutations in human tumors that prevent GSK-3β phosphorylation and thus lead to its aberrant accumulation. E-cadherin, APC, R-spondin and Axin mutations have also been documented in tumor samples, underscoring the deregulation of this pathway in cancer. Wnt signaling has also been shown to promote nuclear accumulation of other transcriptional regulator implicated in cancer, such as TAZ and Snail 1. Furthermore, GSK-3β is involved in glycogen metabolism and other signaling pathways, which has made its inhibition relevant to diabetes and neurodegenerative disorders.

Any number of Wnt activators may be used in the assays of the invention to generate myoblasts. In certain embodiments, a Wnt agonist comprises 5-(Phenylsulfonyl)-N-4-piperidinyl-2-(trifluoromethyl)benzene sulfonamide hydrochloride (WAY-316606), 2-Amino-4-[3,4-(methylenedioxy) benzylamino]-6-(3-methoxyphenyl)pyrimidine (BML-284), (hetero)arylpyrimidines, 2-[2-(4-Acetylphenyl)diazenyl]-2-(3,4-dihydro-3,3-dimethyl-1(2H)-isoquinolinylidene)acetamide (IQ1), (2S)-2-[2-(Indan-5-yloxy)-9-(1,1'-biphenyl-4-ylmethyl)-9H-purin-6-ylamino]-3-phenyl-propan-1-ol (QS11), N-[2-(3,4-dimethoxyphenyl)ethyl]-2-ethyl-5-(phenylsulfonul)benzenesulfonamide, (1-(4-(Naphthalen-2-yl) pyrimidin-2-yl)piperidin-4-yl)methanamine, 3-(2,4-Dichlorophenyl)-4-(1-methyl-1H-indol-3-yl)-1H-pyrrole-2,5-dione, 2-amino-4-[3,4-(methylenedioxy)benzyl-amino]-6-(3-methoxyphenyl)pyrimidine, Dichlorophenyl)-4-(1-methyl-1H-indol-3-yl)-1H-pyrrole-2,5-dione (SB-216763), 6-[[2-[[4-(2,4-Dichlorophenyl)-5-(5-methyl-1H-imidazol-2-yl)-2-pyrimidinyl]amino]ethyl]amino]-3-pyridinecarbonitrile (CHIR99021), (2'Z,3'E)-6-Bromoindirubin-3'-oxime (BIO), 3-[9-Fluoro-2-(piperidin-1-ylcarbonyl)-1,2,3,4-tetrahydro[1,4]diazepino[6,7,1-hi]indol-7-yl]-4-imidazo[1,2-a] pyridin-3-yl-1H-pyrrole-2,5-dione (LY2090314), dichloroacetic acid (DCA) or combinations thereof.

Notch:

Numerous functions have been ascribed to Notch, with some of these helping to explain its cancer-promoting effects in many tissues. Notch helps maintain certain stem cell populations, but interestingly it is also a master regulator of cell fate at critical differentiation branch points in various organ systems. Notch is one of the most powerful of the stem cell-promoting pathways, in conjunction with the Hedgehog and Wnt pathways. Notch seems more likely to play an oncogenic role in cell types that it favors in development and differentiation, such as glial cells or T-cells. Notch activity promotes cell survival and has anti-apoptotic function and numerous mechanisms have been proposed for this. It can also drive cell division in some settings and in some settings may be required for the cell cycle.

Any number of notch inhibitors may be used in the assays of the invention. In certain embodiments, a Notch antagonist comprises gamma-secretase inhibitors (GSIs), alpha-secretase inhibitors (ASIs), N—[N-(3,5-Difluorophenylacetyl-L-alanyl)]-S-phenylglycine t-Butyl ester (DAFT), (5S)-(tert-Butoxycarbonylamino)-6-phenyl-(4R)-hydroxy-(2R)-benzylhexanoyl)-L-leucy-L-phenylalaninamide (GSI L685,458), (s,s)-2-(3,5-Difluorophenyl)-acetylamino]-N-(1-methyl-2-oxo-5-phenyl-2,3-dihydro-1H-benzo[e][1,4]diazepin-3-yl)-propionamide (compound E), dibenzazepine compounds, 7-amino-4-chloro-3-methoxyisocoumarin (JLK6), [11-endo]-N-(5,6,7,8,9,10-hexahydro-6,9-methano benzo[9][8]annulen-11-yl)-thiophene-2-sulfonamide (Compound 18), stapled peptides, peptides, peptidomimetics, antibodies, antibody fragments, enzymes, small molecules or combinations thereof.

Muscular Dystrophy

Muscular dystrophy (MD) is a group of muscle diseases that results in increasing weakening and breakdown of skeletal muscles over time. The disorders differ in which muscles are primarily affected, the degree of weakness, how fast they worsen, and when symptoms begin. Many people will eventually become unable to walk. Some types are also associated with problems in other organs.

The muscular dystrophy group contains thirty different genetic disorders that are usually classified into nine main categories or types. The most common type is Duchenne muscular dystrophy (DMD) which typically affects males beginning around the age of four. Other types include Becker muscular dystrophy, facioscapulohumeral muscular dystrophy, and myotonic dystrophy. They are due to mutations in genes that are involved in making muscle proteins. This can occur due to either inheriting the defect from one's parents or the mutation occurring during early development. Disorders may be X-linked recessive, autosomal recessive, or autosomal dominant. Diagnosis often involves blood tests and genetic testing. There is no cure for muscular dystrophy. Physical therapy, braces, and corrective surgery may help with some symptoms. Assisted ventilation may be required in those with weakness of breathing muscles. Medications used include steroids to slow muscle degeneration, anticonvulsants to control seizures and some muscle activity, and immunosuppressants to delay damage to dying muscle cells. Outcomes depend on the specific type of disorder.

Myotonic.

Also known as Steinert's disease, this form is characterized by an inability to relax muscles at will following contractions. Myotonic muscular dystrophy is the most common form of adult-onset muscular dystrophy. Facial and neck muscles are usually the first to be affected.

Facioscapulohumeral (FSHD).

Muscle weakness typically begins in the face and shoulders. The shoulder blades might stick out like wings when a person with FSHD raises his or her arms. Onset usually occurs in the teenage years but may begin in childhood or as late as age 40.

Congenital.

This type affects boys and girls and is apparent at birth or before age 2. Some forms progress slowly and cause only mild disability, while others progress rapidly and cause severe impairment.

Limb-Girdle.

Hip and shoulder muscles are usually the first affected. People with this type of muscular dystrophy may have difficulty lifting the front part of the foot and as a result may trip frequently. Onset usually begins in childhood or the teenage years.

In boys with DMD, walking abnormalities are a major disease manifestation that has great importance to patients and families. The major goal of medical and physical therapy intervention during the ambulatory phase of DMD is to maintain ambulation for as long as possible. Given that ambulatory compromise is a key component of the DMD disease process and that ambulation measures the function of multiple muscle groups as well as cardiovascular activity, ambulation-related outcome measures are the most relevant endpoints in DMD patients who are still able to walk. The 6-minute Walk Test (6MWT) is feasible, safe, and reliable in boys with DMD who have not yet transitioned to full time wheelchair use. The patients have markedly compromised ambulation relative to healthy boys and correlated 6-minute walk distance (6MWD) with age, anthropometric characteristics, and measures which change with disease progression, including stride length and cadence. In addition, 6MWD can be considered a proxy measure for the energy cost of locomotion in DMD. The 6MWT has been shown to be an integrated global measure of ambulatory function in DMD that is influenced by decreased lower extremity strength, biomechanical inefficiencies during gait, diminished endurance, and compromised cardio-respiratory status. Longitudinal data concerning the 6MWT in DMD have supported the clinically meaningful change in 6MWD to be in the range of 20 to 30 meters, which can serve as the targeted treatment effect in 12-month trials in ambulatory DMD. It appears that a decline of approximately 30 meters from an average performance on the 6MWT in DMD to a threshold 6MWD of <325 meters or <55%-predicted would place a patient with DMD at risk for more precipitous decline in ambulatory function over the subsequent year. Given the limitations of other measures in DMD including surrogate biomarkers, strength by myometry, and timed function tests (TFTs), the 6MWD has become the recommended primary outcome measure in ambulatory DMD. (McDonald, Craig M et al., "The 6-minute walk test and other endpoints in Duchenne muscular dystrophy: longitudinal natural history observations over 48 weeks from a multicenter study" *Muscle & Nerve* vol. 48, 3 (2013): 343-56).

Candidate Therapeutic Agents

In certain embodiments, the candidate agents or potential therapeutic agents increase in vitro fusion rates of, for example, a DMD patient, hiPSC-derived myoblasts as determined by the assays embodied herein.

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Candidate/Test Agents:

Various candidate agents can be employed in the screening methods of the invention, including any naturally existing or artificially generated agents. They can be of any chemistry class, such as antibodies, proteins, peptides, small organic compounds, saccharides, fatty acids, steroids, purines, pyrimidines, nucleic acids, and various structural analogs or combinations thereof. In some embodiments, the screening methods utilize combinatorial libraries of candidate agents. Combinatorial libraries can be produced for many types of compounds that can be synthesized in a step-by-step fashion. Such compounds include polypeptides, beta-turn mimetics, nucleic acids, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. In some methods, prior to examining their ability to disrupt or inhibit Pα-syn* formation in a cell or animal model, combinatorial libraries of candidate agents can be first examined for suitability by determining their capacity to bind to Pα-syn*.

Candidate agents include numerous chemical classes, though typically they are organic compounds including small organic compounds, nucleic acids including oligonucleotides, peptides or antibodies. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries:

Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA*. 91:10779-85, 1994; Lebl et al., One-bead-one-structure combinatorial libraries, Biopolymers 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, Curr Opin Biotechnol. 6:632-9, 1995; Dolle, Discovery of enzyme inhibitors through combinatorial chemistry, Mol. Divers. 2:223-36, 1997; Fauchere et al., Peptide and nonpeptide lead discovery using robotically synthesized soluble libraries, Can J. Physiol Pharmacol. 75:683-9, 1997; Eichler et al., Generation and utilization of synthetic combinatorial libraries, Mol Med Today 1: 174-80, 1995; and Kay et al., Identification of enzyme inhibitors from phage-displayed combinatorial peptide libraries, Comb Chem High Throughput Screen 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., Proc. Nat. Acad. Sci. USA, 90:6909-6913 (1993)); vinylogous polypeptides (Hagihara, et al., J. Amer. Chem. Soc. 114:6568 (1992)); nonpeptidal peptidomimetics with .beta.-D-glucose scaffolding (Hirschmann, et al., J. Amer. Chem. Soc., 114:9217-9218 (1992)); analogous organic syntheses of small compound libraries (Chen, et al., J. Amer. Chem. Soc., 116:2661 (1994)); oligocarbamates (Cho, et al., Science, 261:1303 (1993)); and/or peptidyl phosphonates (Campbell, et al., J. Org. Chem. 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., Nature Biotechnology, 14(3):309-314 (1996) and PCT/US96/10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd., Moscow, RU, 3D Pharmaceuticals, Exton, Pa., Martek Bio sciences, Columbia, Md., etc.).

In some embodiments, a method of identifying candidate therapeutic agents comprises screening a sample containing the specific target molecule in a high-throughput screening assay.

In certain embodiments, a method of screening for candidate therapeutic agents, comprises obtaining fibroblasts from a subject and generating induced pluripotent stem cells (iPSCs); differentiating the iPSCs to generate myoblasts; contacting the myoblasts with a candidate therapeutic agent; culturing the myoblasts with a detectably labeled anti-myosin heavy chain antibody; and, imaging and analyzing the myoblasts generated from the subject's iPSCs as compared to myoblasts generated from a healthy subject's iPSCs.

In another aspect, the invention provides methods for diagnosing or monitoring disease progression in subjects affected by muscular dystrophy. The method comprises obtaining fibroblasts from a subject and generating induced pluripotent stem cells (iPSCs); differentiating the iPSCs to generate myoblasts; culturing the myoblasts with a detectably labeled anti-myosin heavy chain antibody; and, imaging and analyzing the myoblasts generated from the subject's iPSCs as compared to myoblasts generated from a healthy subject's iPSCs. Comparisons of the results over periods of time provides a measure of disease progression and whether a candidate agent is producing therapeutic results. A decrease in in the in vitro fusion rates of the patient hiPSC-derived myoblasts is diagnostic of the disease and/or the severity of disease.

Pharmaceutical Formulations.

The active compounds described herein, e.g. ginsenoside Rd, fenofibrate, a candidate therapeutic agent(s) or combinations thereof, may be formulated for administration in a pharmaceutical carrier in accordance with known techniques. See, e.g., Remington, The Science and Practice of Pharmacy ($21^{st}$ Ed. 2005). In the manufacture of a pharmaceutical formulation according to the invention, the active compound is typically admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

Furthermore, a "pharmaceutically acceptable" component such as a sugar, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as saline solutions, water, emulsions such as oil/water emulsion, microemulsions and various types of wetting agents.

The formulations include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In some embodiments of this invention, the compounds are present in an aqueous solution for subcutaneous administration. In some embodiments, the compounds are provided as a lyophilized powder that is reconstituted and administered subcutaneously.

EXAMPLES

Example 1: Duchenne Muscular Dystrophy hiPSC-Derived Myoblasts Based Drug Screen Identifies Small Molecule Compounds Material and Methods
Animal and Treatment.

All animal experiments were approved by the Institutional Animal Care and Use Committee (IACUC) of The Johns Hopkins University, School of Medicine (Baltimore, Maryland). Mdx$^{5cv}$ (B6Ros.Cg-Dmdmdx-5Cv/J) were obtained from The Jackson Laboratory. Mice were maintained in a 12-h light cycle (7 am-7 pm) with ad libitum access to food and water. Male mdx mice at 3-week-old were randomly assigned to one of the three groups, no treatment, fenofibrate or gensinoside Rd. Mice received either a regular diet of chow or a diet containing fenofibrate (0.1%, w/w, Sigma, St Louis, MO, USA) mixed into the standard chow diet (Global 18% Protein Rodent Diet-Control, Teklad). Ginsenoside Rd was suspended in saline containing 10% 1,3-propanediol as vector. Ginsenoside Rd was provided to mdx mice through Intraperitoneal injection and fenofibrate through diet to age-matched and gender-matched db/m mice for 8 weeks starting at 3 weeks of age.

Generation of DMD Patient's iPSC.

Fibroblasts D2325 was obtained from a DMD patient with the approval of the Johns Hopkins Institutional Review Board. Genetic testing revealed that this patient had a stop codon mutation at c.457. Other fibroblasts were purchased from Coriell Institute for Medical Research (Catalog Number, Camden, NJ, USA) with appropriate Material Transfer Agreement documents. Human cells were cultured in DMEM media containing 10% fetal bovine serum (FBS). Fibroblasts were plated onto 24-well plates and reprogrammed with CytoTune-iPS Sendai Reprogramming Kit (Invitrogen) with the standard protocol. After 9 days, cells were seeded onto MEF feeder layer.

iPSC Differentiation and Myoblasts Maintenance.

The DMD hiPSC-derived myoblasts were differentiated using the CHIR-DAPT protocol (Chal J, et al. (2015) Differentiation of pluripotent stem cells to muscle fiber to model Duchenne muscular dystrophy. *Nat Biotechnol* 33(9): 962-969). Briefly, hiPSCs were plated as single cells on Geltrex (Gibco) treated dishes, at a density of $1.5 \times 10^5$ cells per well in a 24-well plate, in the presence of MEF-conditioned N2 media containing 10 ng/ml of FGF-2 (PeproTech) and 10 µM of Y-27632 (Cayman). The cells were induced to differentiate into myoblasts by adding CHIR99021 (3 µM) in N2 medium for 4 days and by DAPT (10 µM) for the following 8 days. Cells continued to differentiate and mature in N2 medium for the next 13 days. Myoblasts were collected by FACS with the selection marker NCAM+/HNK1− (NCAM:5.1H11, DSHB; HNK1: C6680, Sigma).

The NCAM+/HNK1− myoblasts were maintained in a humidified incubator containing 5% $CO_2$ at 37° C. and grown in N2 media supplemented with 10% FBS. To induce myotube formation, expanded NCAM+/HNK1− myoblasts were plated to confluence, and switched to N2 media without serum.

Drug Screen.

The FACS-sorted DMD-hiPSC-derived myoblasts were seeded at 25,000 cells per well in 96 well plates. Medium was changed to N2 without additional serum and cells were treated with compounds from the Johns Hopkins Clinical Compound Library (JHCCL v1.3) (1 µM), DMSO (0.1%, negative control) or gentamicin (500 µg/ml, Sigma) every 3 days for 9 days. The compound library consisted of 1,524 small molecules. Cells were then fixed with 4% PFA and stained with Myosin Heavy Chain antibody (MyHC). Automated image acquisition protocol with high content imaging/analyzing system (BD Pathway 855, available at ChemCore, JHSOM), and automated analysis programming (BD AttoVision) were used to image and analyze myotube formation. Primary hits were validated in secondary replicate experiments (n=3), and statistical significance was determined by one-way ANOVA with post-hoc Tukey Test for comparing multiple treatments Western Blot.

Whole-cell extracts were prepared by lysing cells on plate with RIPA buffer (CST) supplemented by proteinase inhibitor and phosphatase inhibitor cocktail (CST). Western blotting was performed according to the standard protocol using precast NuPAGE (4-12%) Bis-Tris gel (Invitrogen). Protein transfer was performed with the Bio-Rad turbo or wet/tank blotting system. Nitrocellulose membranes were incubated with primary antibodies overnight at 4° C. Membranes were then incubated with a secondary IRDye 800 conjugated anti-rabbit IgG, or Alexa Fluor 680 anti-mouse IgG and proteins were visualized and quantified using the LI-COR Odyssey Infrared Imaging System (LI-COR). Primary antibodies applied in this study were all purchased from Cell Signaling Technology except for the MEF2C antibody, which was from Sigma.

Affymetrix Microarray and qPCR.

Triplicate samples were used in microarray analysis. D2 hiPSC derived myoblasts were treated with ginsenoside (5 µM), fenofibrate (8 µM) or DMSO for 24 h in the differentiation medium. RNA was isolated using TRIzol (Invitrogen Life Technologies, Carlsbad, CA) followed by purification and DNase digestion using RNeasy mini kits (Qiagen, Venlo, Netherlands) according to manufacturer's instructions. Quantification of total RNA was performed on a Nanodrop spectrophotometer (Thermo Scientific) and RNA quality was tested on an Agilent TapeStation with R6K ScreenTapes (RIN 7.6-9.8). Generation of sense strand cDNA from purified total RNA was followed by second strand synthesis, in vitro transcription cDNA synthesis, and single stranded cDNA synthesis and RNA hydrolysis. Fragmentation and labelling were performed according to manufacturer's instructions (GeneChip WT Plus reagent kit, Affymetrix, Santa). RNA extraction and qPCR were performed according to previous protocols, and primers are included in Table 1. The microarray data has been deposited in NCBI's Gene Expression Omnibus database and is accessible through the GEO series accession number GSE121023.

Treadmill and Grip Strength.

Forelimb grip strength was measured as maximal tensile force using a computerized force transducer (Grip Strength Meter, Bioseb). Five measurements were performed for each animal and the maximum value was used for the analysis. Treadmill testing was performed using a motor-driven treadmill (Columbus Instruments). Prior to the test day, acclimatization was performed 5 times over a period of 2 weeks at 10 m/min. On the test day, mice ran at 5 m/min for 5 min (warm up) and the speed was increased 1 m/min every min up to 10 m/min. Mice were considered exhausted when they sat for more than 10 sec on a shock pad for the third time.

Evans Blue Staining and Histology Analysis.

Gastrocnemius, tibialis anterior, and diaphragm muscles were embedded in OCT, frozen in isopentane, and cross-sectioned (~2-10 μm thickness). The sections were also stained with DAPI to visualize nuclei. In mice where Evans blue dye (EBD, 10 mg/ml) was used to evaluate membrane damage, EBD was injected at 0.05 ml/10 g intraperitoneally, 24 hours before sacrificing the mice. To evaluate EBD staining, gastrocnemius muscle sections were fixed with acetone and imaged with fluorescence microscopy. The area of EBD as a percentage of total area was calculated. To evaluate the number of central nucleated fibers, sections of the tibialis anterior muscle were stained with hematoxylin and eosin. Central nucleated fiber number was counted and analyzed against total fiber number. Diaphragm sections (10 μm) were stained with Masson's trichrome to determine collagen content. The stained areas were quantified against the total area.

In vivo muscle physiology. Quadriceps strength (maximal isometric torque) and susceptibility to injury were assessed in vivo as described (69, 70). Briefly, animals were anaesthetized with 3-5% isoflurane and placed in a supine position. The thigh was stabilized and the ankle was secured on to a lever arm. The knee was aligned with the axis of the stepper motor (model T8904, NMB Technologies, Chatsworth, CA, USA) and a torque sensor (QWFK-8M, Sensotec, Columbus, OH, USA), and the femoral nerve was stimulated via subcutaneous needle electrodes. A custom program based on commercial software (LabView version 8.5, National Instruments, Austin, TX, USA) was used to synchronize contractile activation and the onset of forced knee flexion. The position of the leg that results in optimal muscle length has been previously described and maximum isometric torque was measured in Newton-millimeters (Nmm). Injury was induced by 15 forced lengthenings (knee flexion) superimposed onto maximal quadriceps contractions through a 40-100 degree arc of motion (with full knee extension considered 0 deg) spaced 1 min apart. Loss in maximal isometric torque was measured 5 min after the last lengthening contraction. Since the knee position, lever arm, and moment arm of the muscle are unchanged between tests, maximal isometric torque reflects maximal isometric muscle force.

Tibialis anterior muscle strength (maximal isometric force) and rate of fatigue were measured. Briefly, animals were anaesthetized with 3-5% isoflurane and placed in a supine position. The tibia was stabilized and the distal tendon of the tibialis anterior (TA) was surgically released and attached to the load cell (FT03, Grass Instruments, Warwick, RI). The load cell was adjusted via a micromanipulator to stretch the muscle to resting length (aka, optimal length). TA contraction was then triggered via subcutaneous stimulation of the fibular nerve, and the resulting force generated was sampled at 1 kHz and analyzed with acquisition software (PolyVIEW™ 16, Grass Instruments). After contractile function experiments, animals were euthanized and the TAs were harvested and weighed. As muscle length was fixed in all experiments, and muscle density is assumed to be a constant, physiological cross-sectional area of the TA was solely a function of muscle mass. Force was therefore normalized to TA mass to calculate as specific force (g/g). To provide an index of fatigue, muscle tension was measured after 5 minutes of tetanic stimulation (200 ms train duration) repeated at 1 Hz and expressed as a percentage of initial tension.

Blood Content Analysis.

Mdx mouse blood samples were collected by cardiac puncture. Serum samples were separated with microvette CB 300 (Sarstedt). Plasma samples were collected using microtainer, and plasma analyses were carried out at the Phenotyping and Pathology Core at the Johns Hopkins University School of Medicine. Serum triglyceride and cholesterol levels were measured with an infinity kit (Thermo Fisher Scientific, Middletown, VA). Non-esterified free fatty acids were measured with a NEFA-HR (2) kit (Wako Chemicals, Richmond, VA).

Statistical Analysis.

All data are shown as mean±SEM and were subjected to statistical analysis. Significance was analyzed by one-Way ANOVA using Dunnett's, Tukey's multiple comparison test or were analyzed by two-tailed unpaired Student's t-test. The 'n' values indicate the number of independent biological samples. Data were analyzed and represented with Graph-Pad Prism. Investigators were blinded to allocation during experiments and outcome assessment, except for when blinding was not possible.

Results

Primary Screening of a Small Molecule Compound Library with DMD Patient hiPSC-Derived Myoblasts.

Figure 5A:
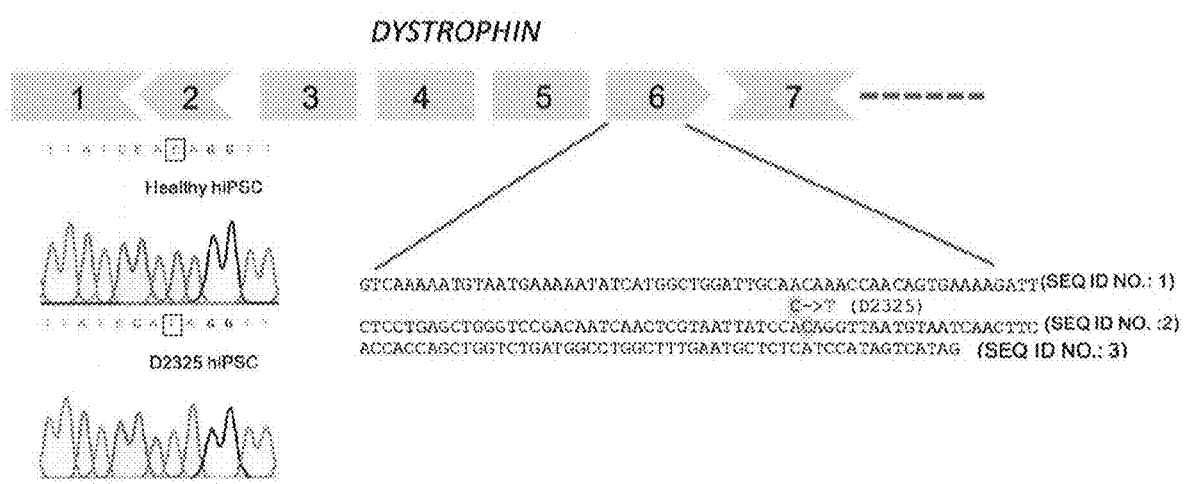
FIGS. 5A-5C are a series of a schematic representation (FIG. 5A), an immunofluorescent image (FIG. 5B) and a graph (FIG. 5C), showing the phenotype of DMD hiPSC-derived myoblasts.
Figure 5B:
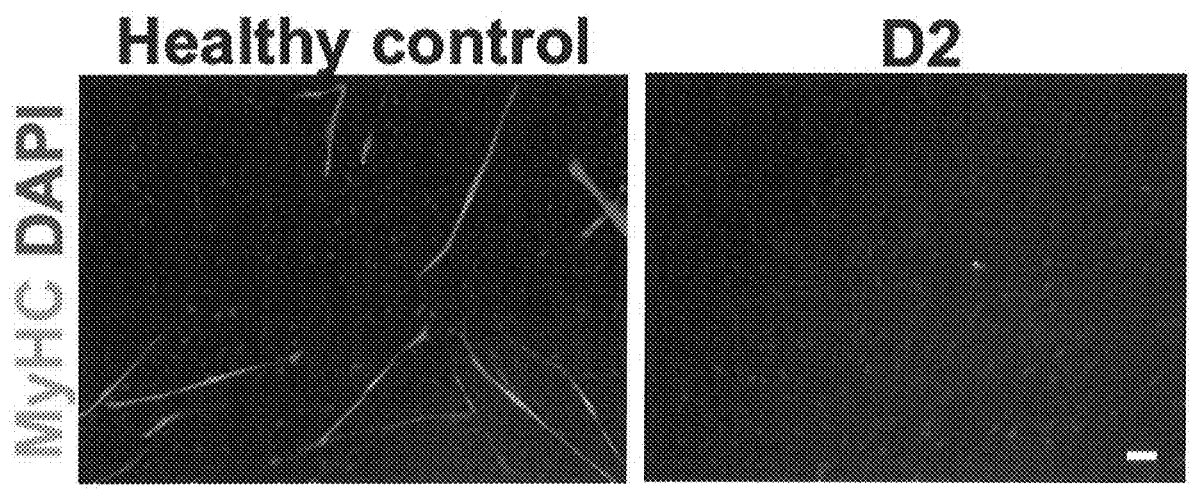
Figure 5C:
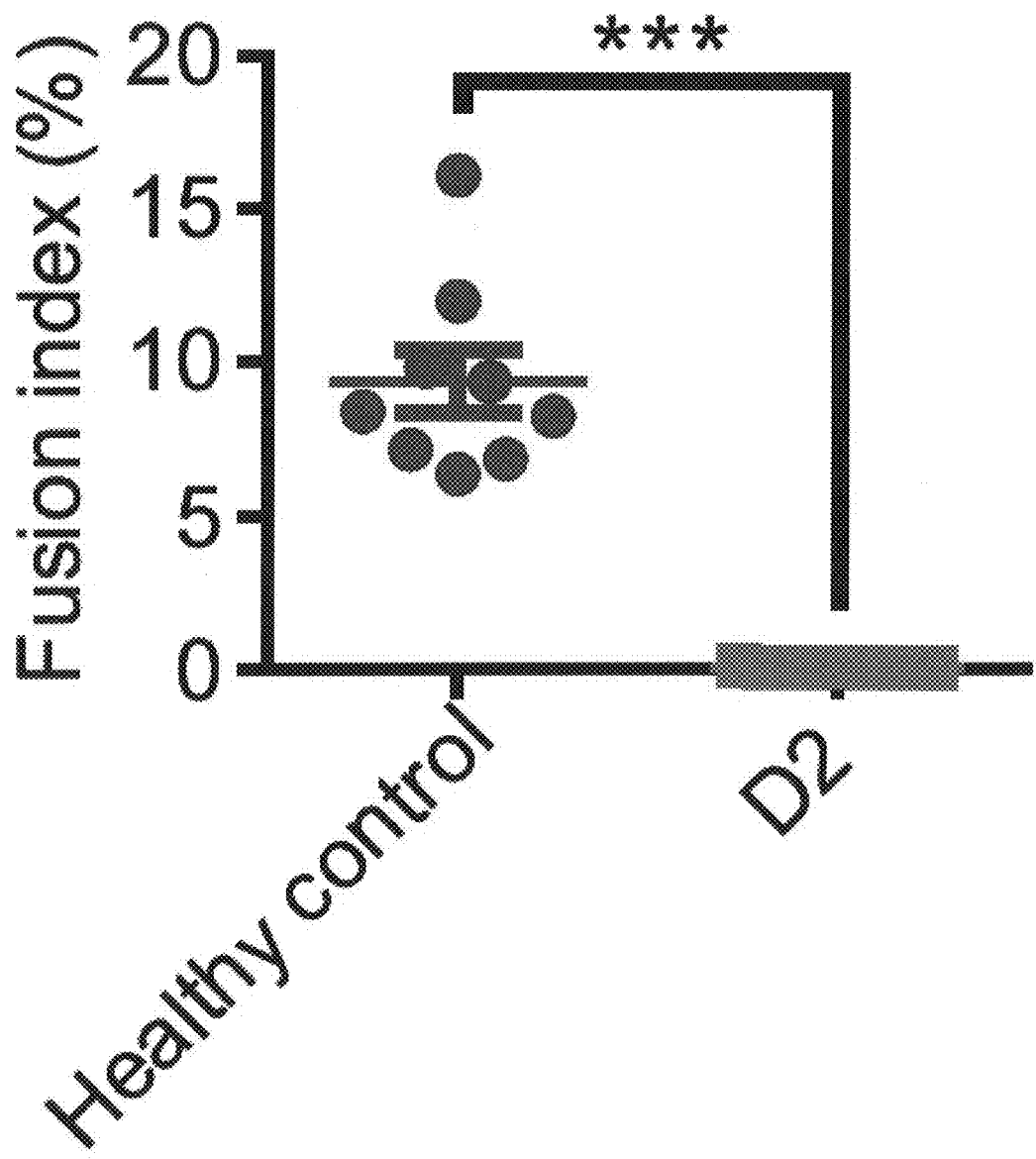

DMD-patient-derived myoblasts were generated from hiPSC in a chemically defined system of Wnt activation and Notch inhibition (Choi I. Y, et al. (2016) *Cell Reports* 15(10):2301-2312) and used patient-specific myoblasts that were derived from D2325 hiPSC line of a DMD patient (hereafter D2 myoblast) whose DMD gene encoding dystrophin carried a nonsense mutation (c.457 C→T) (FIG. 5A). Compared with the healthy hiPSC-derived myoblasts, D2 myoblasts formed very few myotubes based on myosin heavy chain (MyHC) antibody staining (FIGS. 5B-5C). These data were consistent with the inventors' previous studies, in which myoblasts derived from multiple DMD-hiPSC lines with various DMD gene mutations formed significantly fewer myotubes, based on MyHC staining (Choi I. Y, et al. (2016); Chal J, et al. (2015). *Nat Biotechnol* 33(9):962-969; Blau H M, et al., (1983). *Proceedings of the National Academy of Sciences of the United States of America* 80(15):4856-4860), an observation also made in primary myoblasts of DMD patients (Jasmin G, et al. (1984). *Lab Invest* 50(2):197-207; Delaporte C et al. (1984). *J Neurol Sci* 64(2):149-160). Inefficient myotubes formation was partially reversed by a known stop-codon read-through compound, gentamicin (FIG. 2A) (Barton-Davis E R, et al. (1999) *The Journal of Clinical Investigation* 104(4):375-381). Although not used in the clinical setting due to an unfavorable risk/benefit profile (Malik V, et al. (2010). *Annals of Neurology* 67(6):771-78021), gentamicin provided a positive control in the screen. To test the feasibility of the compound screening format, myoblasts treated with gentamicin or vehicle control (DMSO) were imaged and analyzed by High-content imaging analysis system (BD pathway 855) that could detect and outline the MyHC positive cells (FIG. 1A). A variety of parameters were compared after the treatment of gentamicin or vector DMSO on D2 myoblasts in differentiation condition. It was found that when Average Length of Cells which describes the length of each outlined object was considered, statistically distinguishable values between positive and negative controls (Z'=0.59) (FIG. 1C) were obtained. MyHC immunofluorescent intensity was also considered as it is a myotube marker and measuring its protein expression is a hall mark for myotube formation (Schiaffino S, et al. (2015) *Skelet Muscle* 5:22). However, as the background noise was higher in MyHC measurement, the impact on its value was reduced by 70%. Therefore, when both cell average length and MyHC intensity were taken into account, it is still a valid readout (Z'=0.58) (FIG. 1B). To minimalize the plate to plate variation, the values obtained from each tested compound were normalized to positive and negative controls. Thus, algorithm 1 as equation: normalized Cell ave length+ 0.3*MyHC intensity. Also, in order to not exclude the compounds that can restore the myotube shape without increasing the MyHC immunofluorescent intensity, absolute values of cell average length (without normalization) were used as algorithm 2. Algorithm 2 also helps to eliminate the compounds that are auto-fluorescent.

Figure 1D:
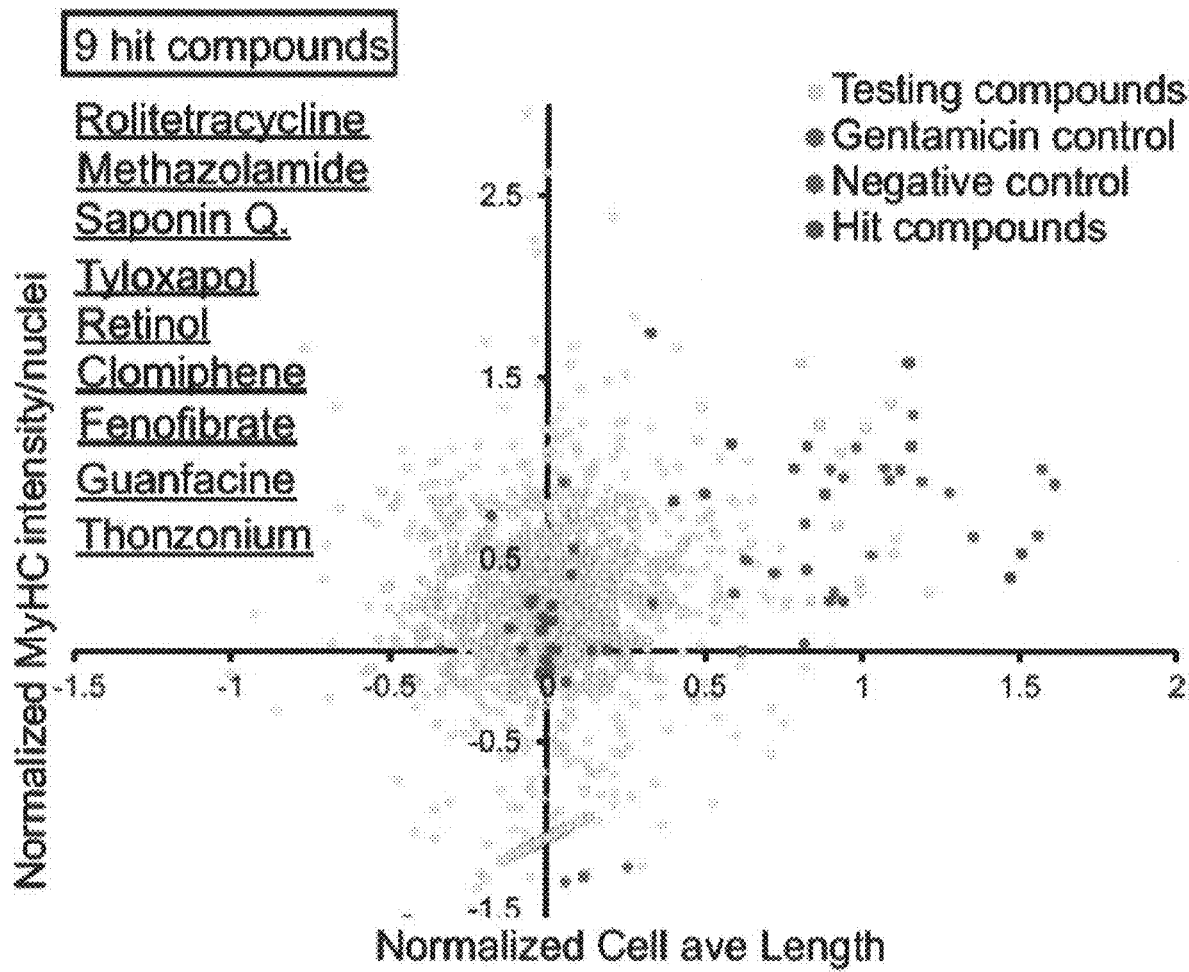
Figure 6A:
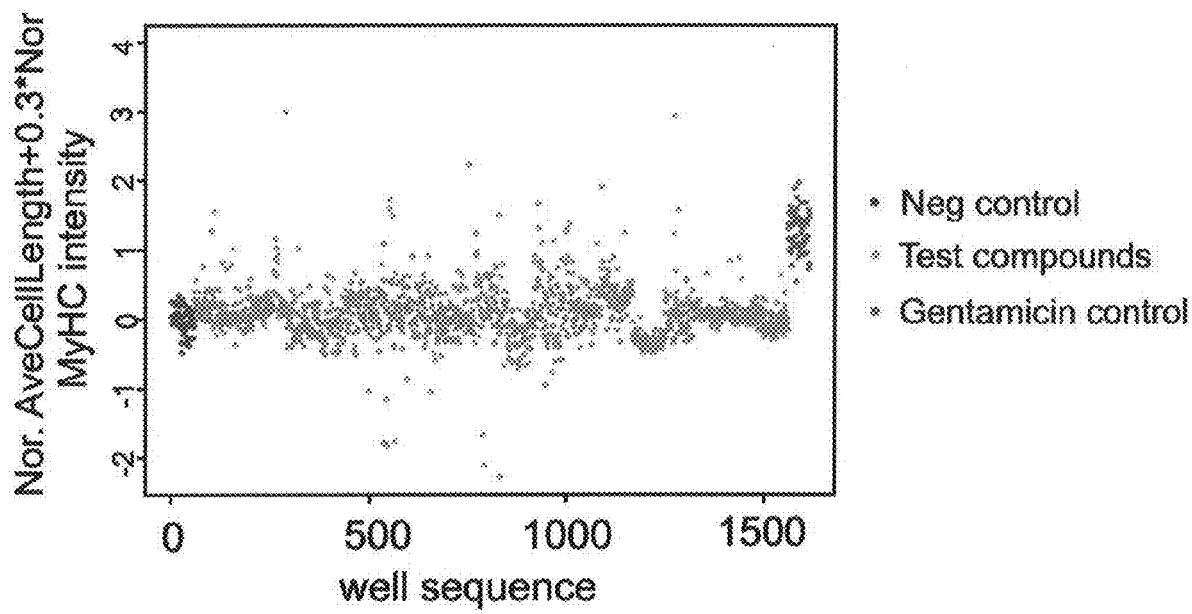
FIGS. 6A and 6B are scatter plots showing the result of two algorithm of D2 myoblasts treated by the JHCCL compound library. Algorithm 1 (FIG. 6A) and algorithm 2 (FIG. 6B) plot of all tested compounds along with DMSO (blue) and gentamicin (red) treated D2 cells.
Figure 6B:
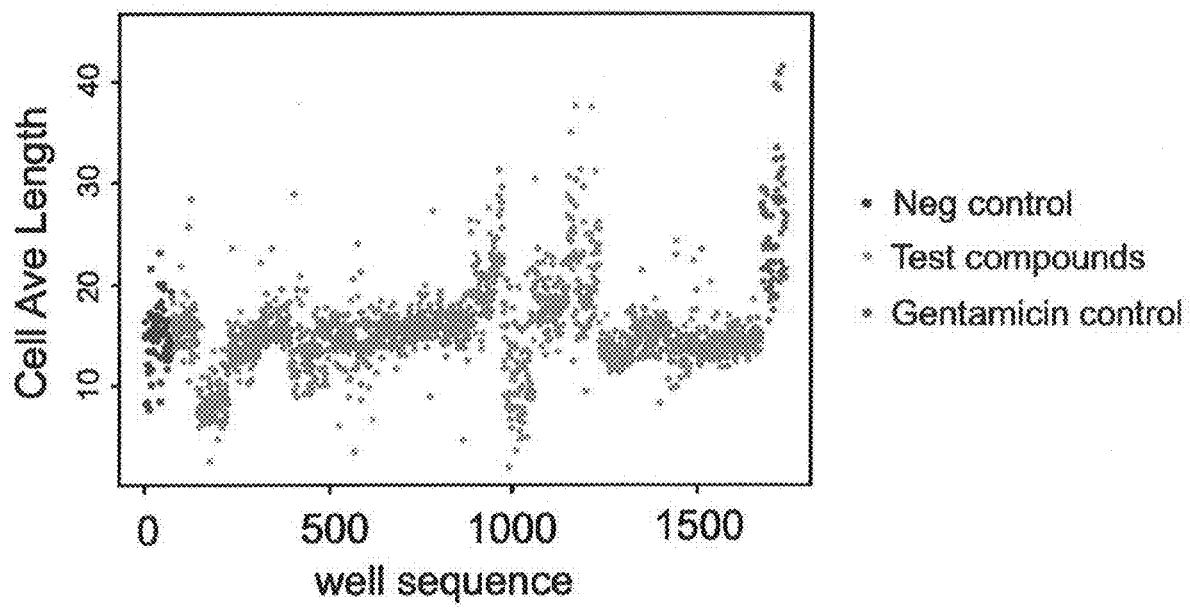

After cell plating conditions were optimized (see Materials and Methods), D2 myoblasts were seeded onto 96-well plates and screened with 1,524 small molecule compounds from the Johns Hopkins Clinical Compound Library (v 1.3), which contains both FDA- and foreign-approved drugs (Chong C R, et al. (2006) *Nat Chem Biol* 2(8):415-416). The compounds in the library are structurally diverse and some of them are natural compounds. Therefore, they are suitable for drug repurposing for rare diseases. Compounds that had values of Algorithm 1 above the average value of gentamicin-treated myoblasts were selected (FIG. 6A). The absolute value of the cell average length (FIG. 6B) was also used to select candidate compounds that had the highest values of each plate. The compounds that fulfilled both criteria by both Algorithm 1 and Algorithm 2 included 9 compounds which showed distinctive value from negative controls and aligned with the gentamicin group (FIG. 1D).

Two out of nine hit compounds (methazolamide and clomiphene) have previously been reported to ameliorate the disease phenotype of the mdx mouse model. Methazolamide was identified in a drug screening of the *C. elegans* model and it was shown to increase the tetanic force in mdx mice. Clomiphene is an analog of tamoxifen that was shown to increase force production and suppress fibrosis in mdx mice. The identification of methazolamide and clomiphene by these two algorithms supported the validity of the screening efforts and data analysis.

Secondary and Tertiary Screen to Obtain 2 Final Hit Compounds.

Figures 2A, 2B, 2C:
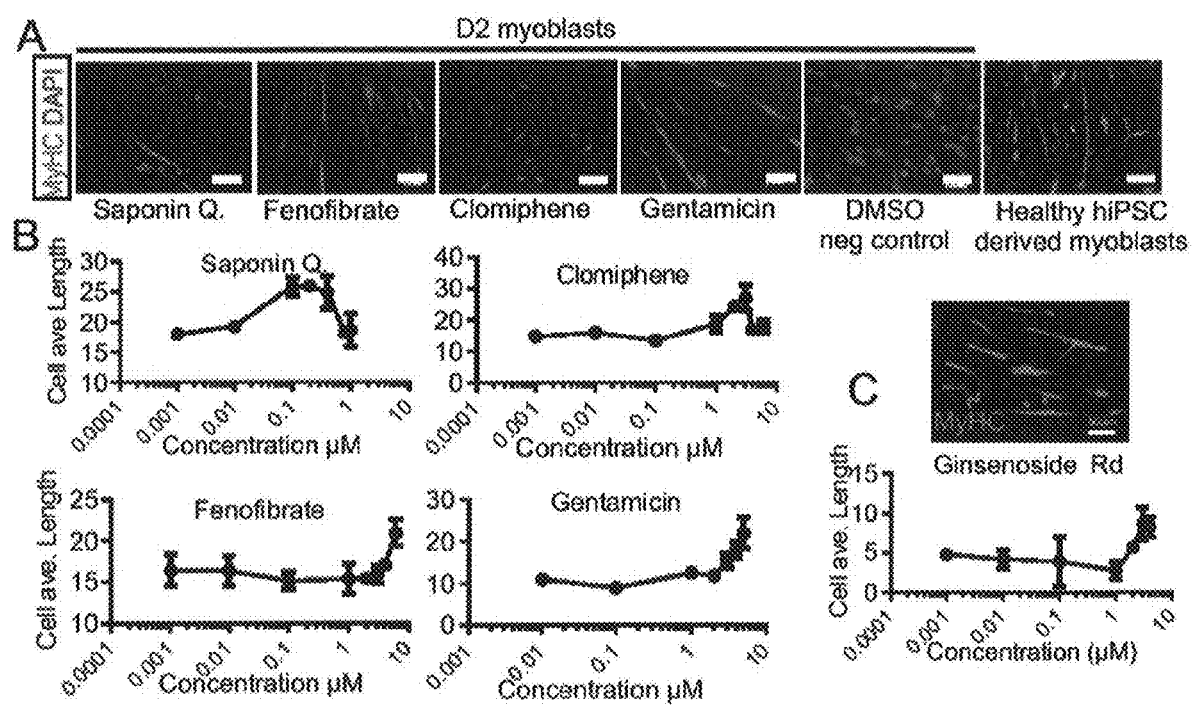
FIGS. 2A-2F are a series of fluorescent stains, graphs and blots demonstrating that secondary and tertiary screening narrowed the list of candidate compounds down to final two hits.
Figures 2D, 2E, 2F:
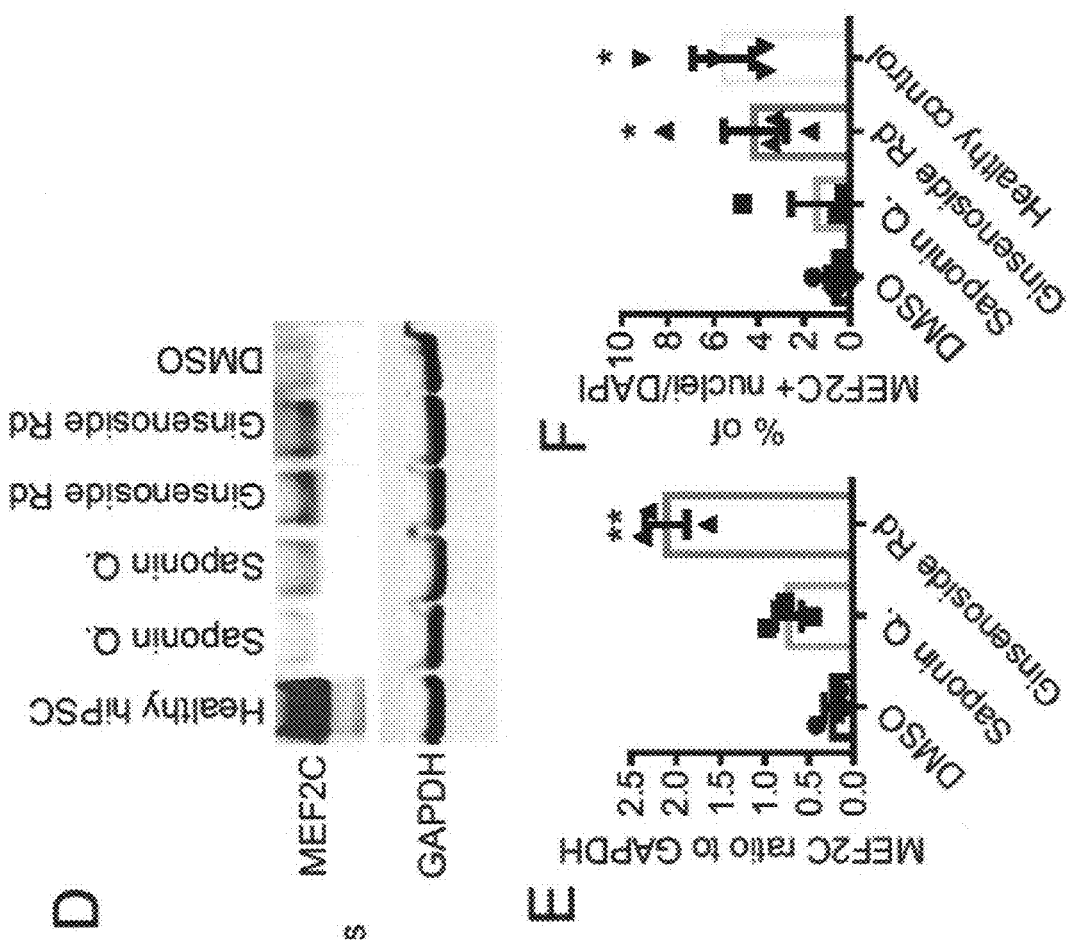
Figures 7A, 7B:
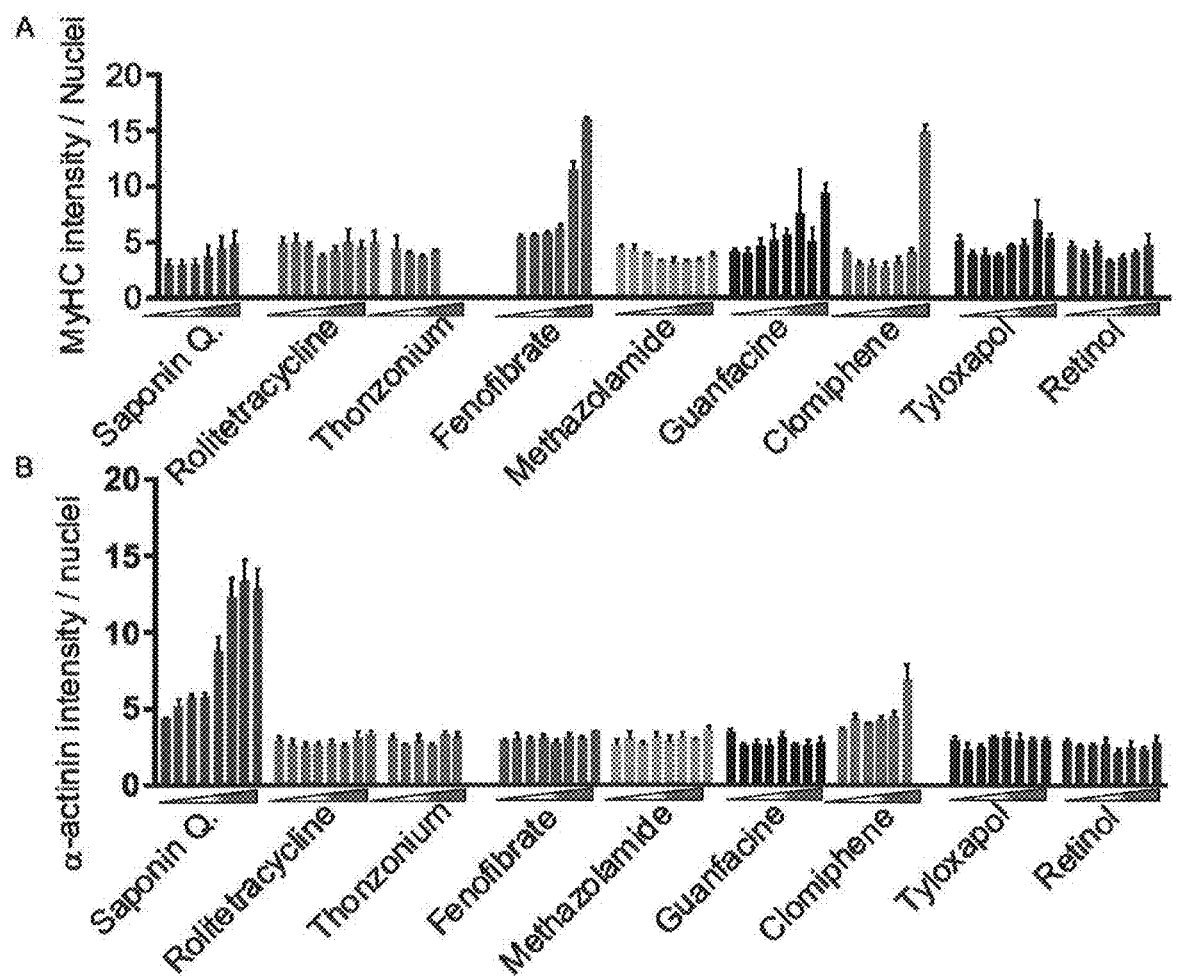
FIGS. 7A-7G are graphs showing the dose-response of 9 hit compounds and analogs of Saponin Q and fenofibrate.
Figures 7C, 7D, 7E:
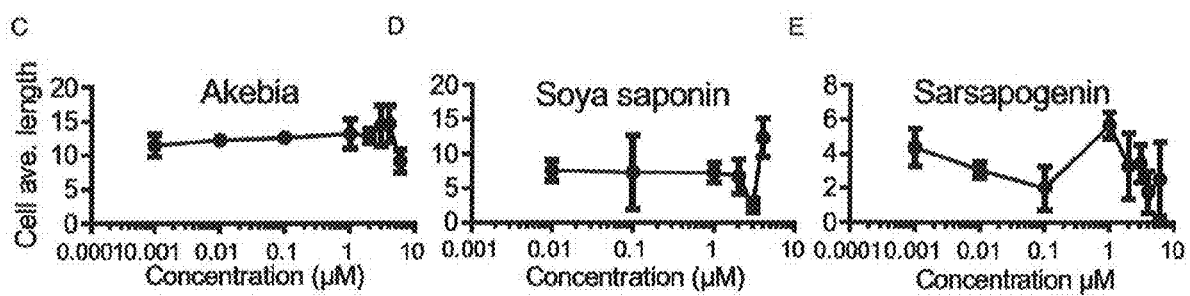
Figures 7F, 7G:
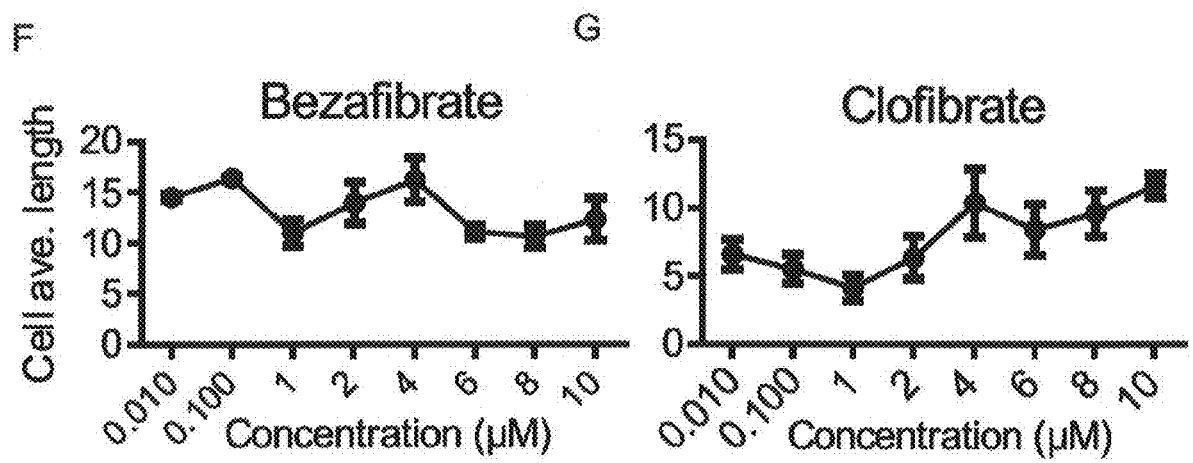
Figure 8A:
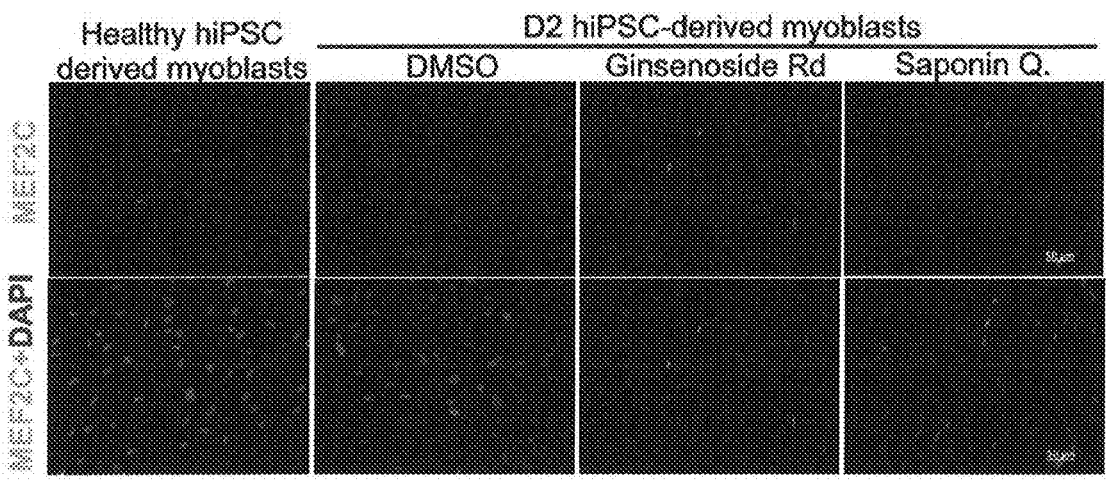
FIG. 8A is a series of representative immunocytochemistry images of MEF2C antibody labeled healthy hiPSC derived myoblasts or D2 cells that were treated with DMSO, ginsenoside Rd or saponin Q, scale bar=50 μm.
Figure 8B:
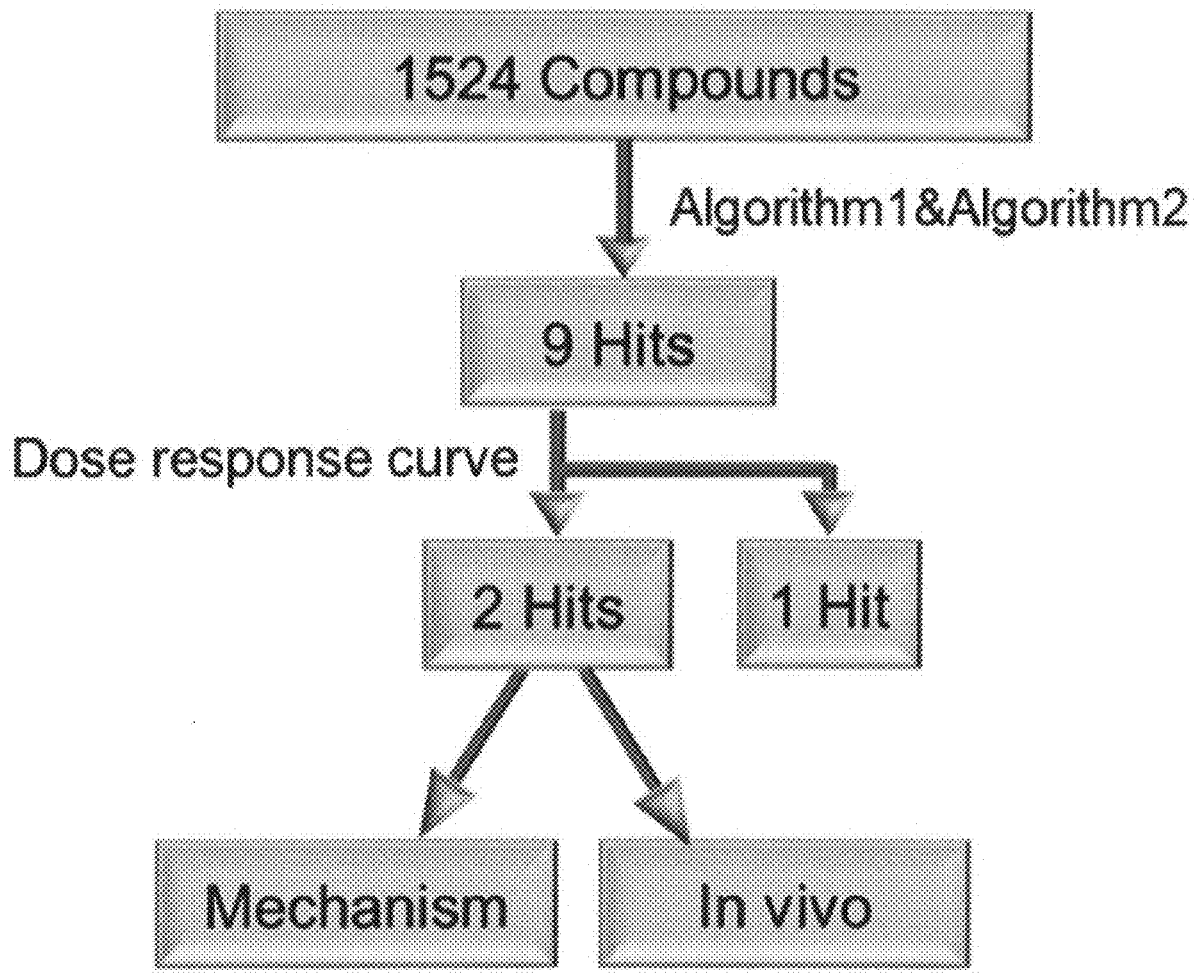
FIG. 8B: is a flow chart of the tiered compounds screen.

To further evaluate the efficacy of the 9 hit compounds and determine their optimal concentrations, an 8-point dose response assay was conducted, based on three parameters: anti-MyHC immunocytochemistry, anti-α-actinin immunocytochemistry and average cell length (FIGS. 7A-7B). The final hit compounds were determined by their ability to generate does-dependent response curve with at least two of the above three parameters. Based on that, three hit compounds were selected—clomiphene, saponin Q. (saponin from quillaja bark) and fenofibrate (FIG. 2B, FIGS. 7A-7B). As the analog of clomiphene, tamoxifen, has been discovered and is already under clinical trial, Saponin Q. and fenofibrate were selected for further analysis. However, Saponin Q. has relatively high toxicity among all members in the saponin family and thus cell death was observed after a high concentration treatment of saponin Q. To find alternative natural products that were less toxic, 4 analogs of saponin (akebia, soya saponin, sasarpogenin and ginsenoside Rd) were tested (FIG. 2C, FIG. 7C-7E). Among them, ginsenoside Rd treatment not only showed a dose-dependent effect on D2 myoblasts, but also increased the levels of MEF2C protein expression as detected by both Western blots, whereas saponin Q. did not (FIGS. 2D-2E). Immunocytochemistry confirmed the above result by showing that upon ginsenoside Rd treatment, there were more MEF2C expressing cells compared with vector control (FIG. 2F, FIG. 8A). Therefore, ginsenoside Rd holds advantages over saponin Q. not only due to its lower toxicity, but also because it induces MEF2C protein expression, which is critical for myogenic differentiation. As a result, the selected final lead compounds were fenofibrate and ginsenoside Rd (FIG. 8B).

TGF-Beta and ERK1/2 Signaling Pathways Play Key Roles in Improving Myotube Formation of Dystrophin Deficient Myoblasts.

Figure 9A:
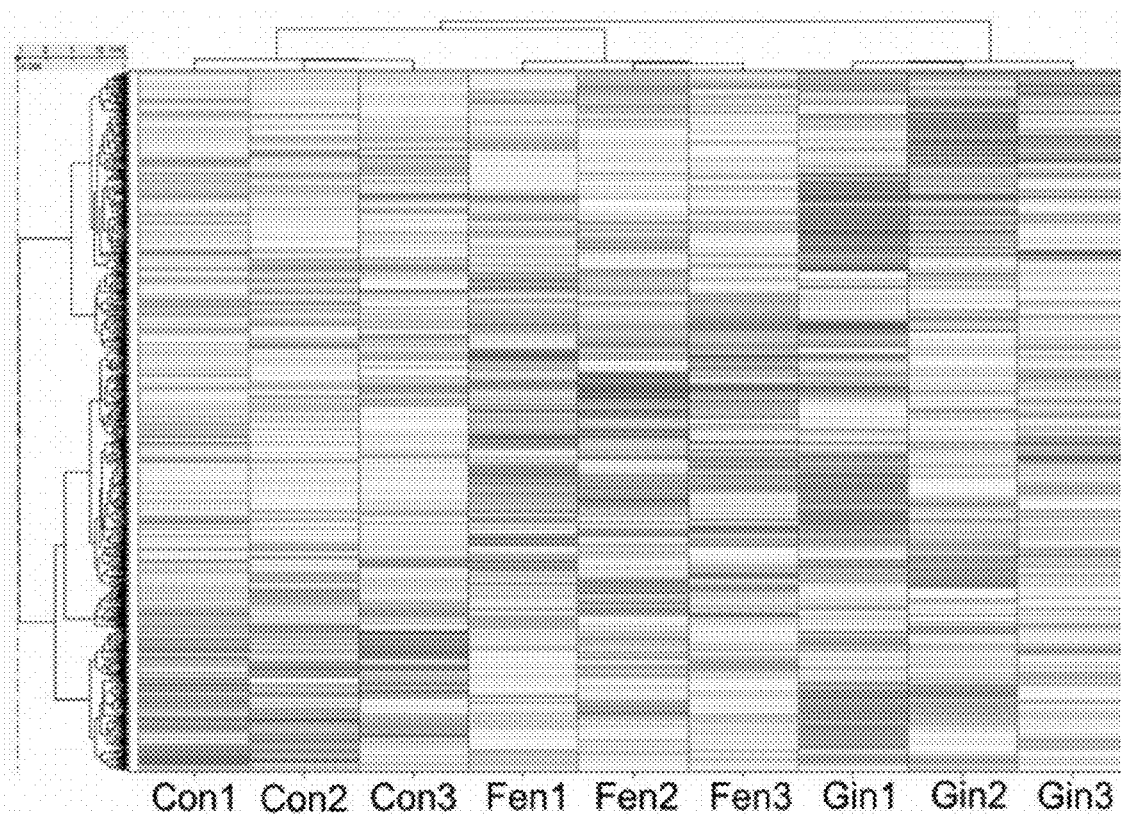
FIGS. 9A-9C show a heatmap and plots demonstrating the gene expression profiling by microarray. (A) Heat map of gene expression level in D2 myoblasts treated by DMSO (control), fenofibrate (fen) and ginsenoside Rd (gin) showing how treatment with each compound results in distinct gene expression changes, n=3.
Figure 9B:
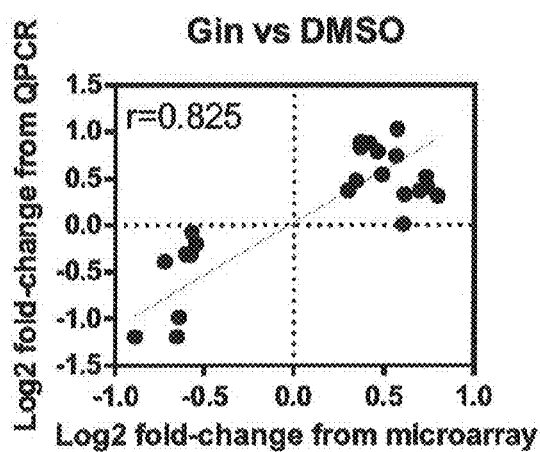
Figure 9C:
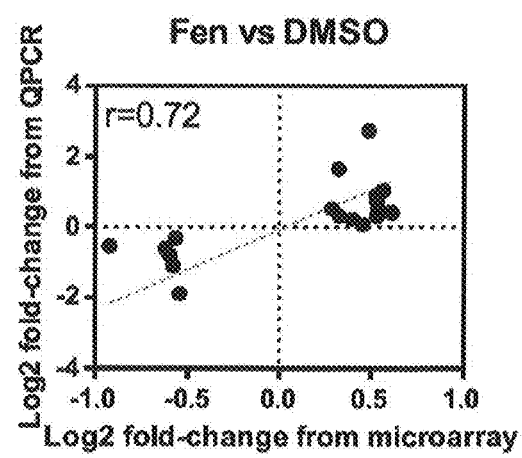

In order to elucidate the mechanism whereby the two final hit compounds ameliorate fusion defects of the D2 myoblasts, an unbiased global transcriptional profile was performed on D2 myoblasts treated with either fenofibrate (fen, 8 µM) or ginsenoside Rd (gin, 5 µM). The heat map showed distinctive gene expression profiles among groups (FIG. 9A), and the transcriptional analysis results were validated by qRT-PCR (27) (FIG. 9B-C). The ingenuity pathway analysis shows that the most significant positive correlation (z-score>2) after ginsenoside Rd treatment is with the FLT3 signaling pathway (FIG. 3A). It has been reported that FLT3 regulates myogenic differentiation by enhancing the expression of p21 (WAF1/CIP1), a cell cycle inhibitor, resulting in cells exiting the cell cycle. Increased levels of p21 were detected in D2 myoblasts under the treatment of FLT3 and this effect was also seen in ginsenoside Rd-treated D2 myoblasts (FIGS. 3B-3C). At the same time, ERK1/2, a known FLT3 pathway downstream effector, was activated both by FLT3 recombinant protein and ginsenoside Rd in D2 myoblasts (FIGS. 3D-E). As for fenofibrate, it was shown to suppress TGF-β signaling in D2 myoblasts (z-score<−2 in the pathway analysis. Indeed when fenofibrate was applied to D2 myoblasts together with TGFβ1 recombinant protein, SMAD2/3 phosphorylation was reduced, indicating fenofibrate suppressed TGF-β signaling (FIG. 3F-G) (Derynck R & Zhang Y E (2003) *Nature* 425(6958):577-584.). As TGF-β signaling plays a suppressive role in muscle differentiation, it is likely that fenofibrate improves D2 myoblasts differentiation/fusion efficiency by inhibiting TGF-β. From the above results, it was concluded that the positive effects of ginsenoside Rd and fenofibrate are associated with the FLT3 and TGF-β pathways, respectively.

Ginsenoside Rd and Fenofibrate Ameliorate the Disease Phenotype of the Mdx Mouse Model of DMD.

Figures 4A, 4B, 4C, 4D:
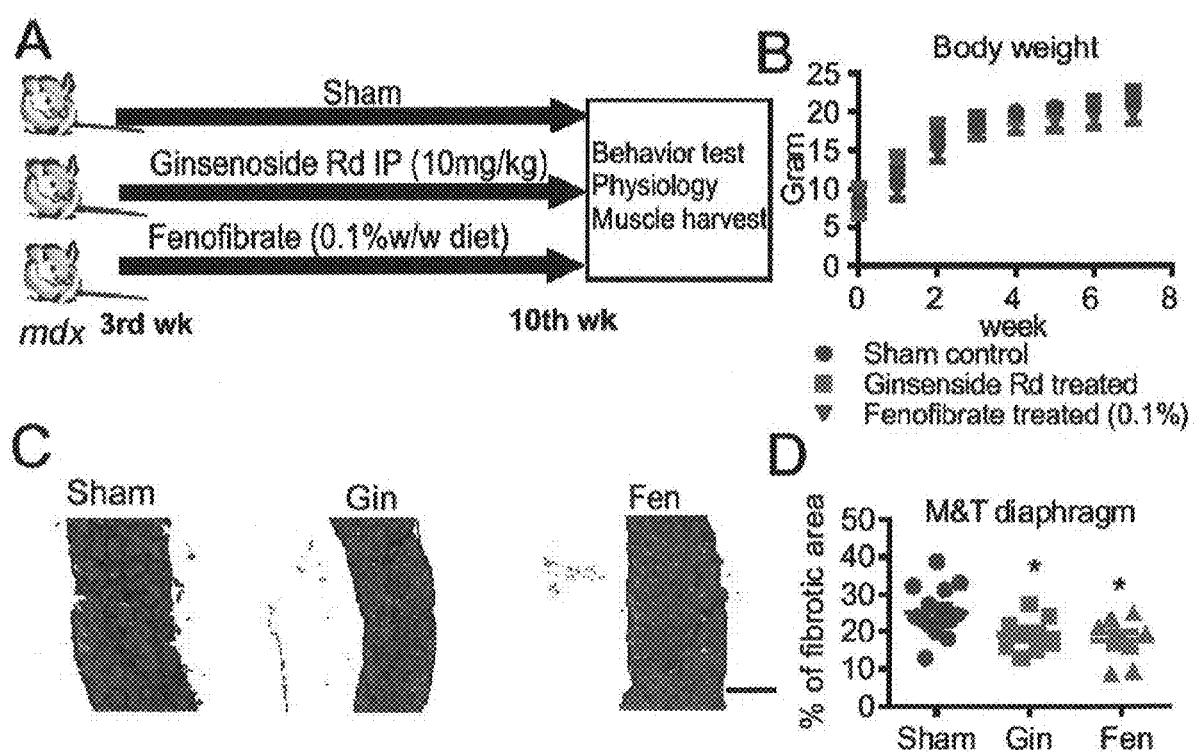
FIGS. 4A-4F are a series of illustrations, blots and graphs showing Ginsenoside Rd (gin) (10 mg/kg) and fenofibrate (fen) (0.1% w/w) treatment ameliorate the disease symptom of mdx$^{-5cv}$ mice.

Since ginsenoside Rd and fenofibrate were effective in correcting the in vitro DMD phenotype of DMD hiPSC-derived myoblasts, it was sought to determine if they also had a therapeutic effect in vivo. Therefore, each of the two compounds were tested in $mdx^{5cv}$ mice, which carry a nonsense mutation in exon 10 of the DYSTROPHIN gene, causing a frameshift deletion in the encoded mRNA (Delaney K, et al. Cell Biology international 41(7):706-715). Ginsenoside Rd (10 mg/kg) was administered through daily intraperitoneal injection and fenofibrate (0.1% w/w) through diet beginning postnatal day 21, for 8 weeks (FIG. 4A). Neither of the compounds affected the growth curve of the mdx mice (FIG. 4B). Fenofibrate lowered the level of triglyceride while increasing high-density lipoprotein (HDL) and cholesterol in the blood (FIGS. 10E-10G). At the end of the treatment period, the pathology of different muscles was assessed. Skeletal muscle fibrosis is most prominent in the diaphragm of young mdx and the levels of fibrosis in diaphragm were reduced by the treatment of ginsenoside Rd (29%) and fenofibrate (42.1%) (FIG. 4C-D).

Figures 4E, 4F, 4G, 4H:
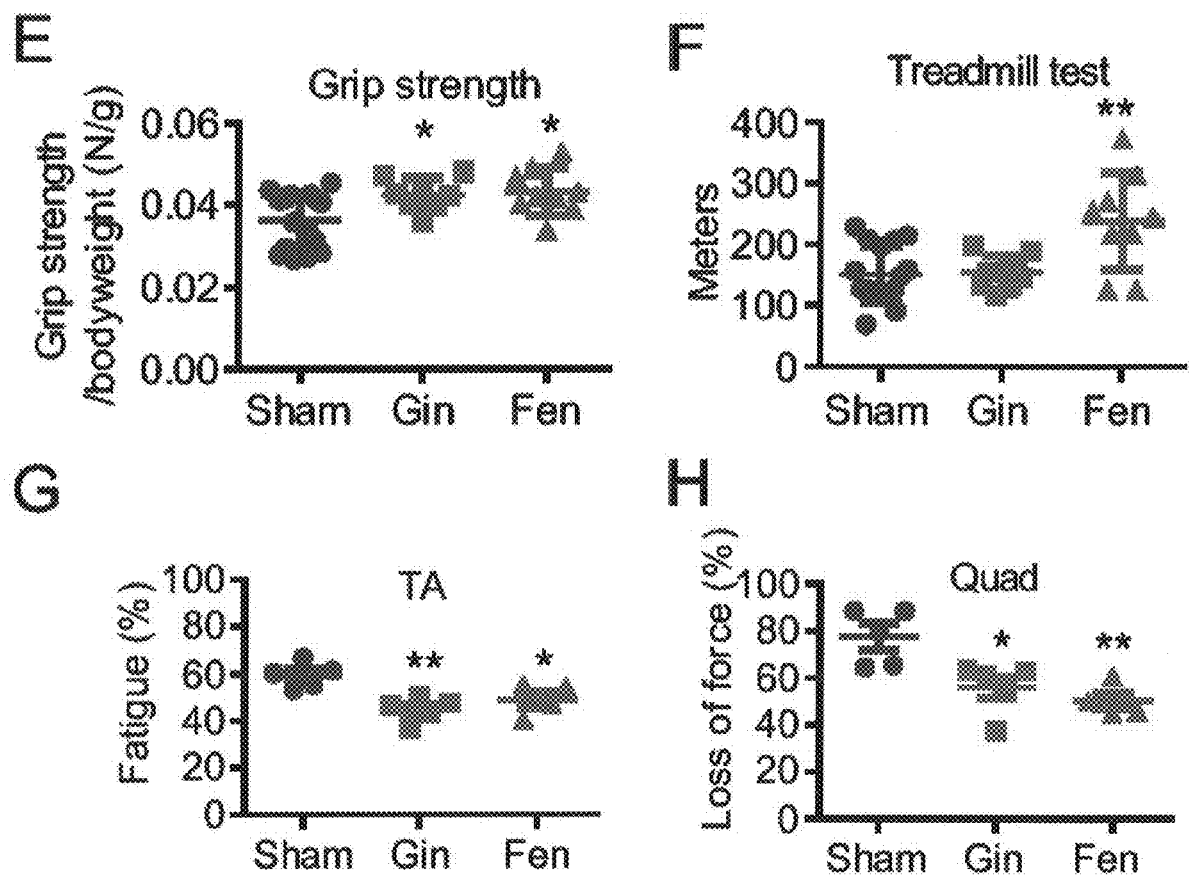
FIG. 4G: Fatigue index (%) represents the reduction in maximal tetanic tension measured after 5 minutes of repeated tetanic stimulation at 1 Hz in TA muscle of mdx mice, n=5 for all 3 groups.
FIG. 4H: Susceptibility to injury (percent loss of maximal isometric force after lengthening contractions) of quadriceps muscle, n=5 for all 3 groups. *P≤0.05, **P≤0.01. (Data=Mean±SEM, one-way ANOVA with Dunnett's multiple comparison test with sham control).
Figure 10A:
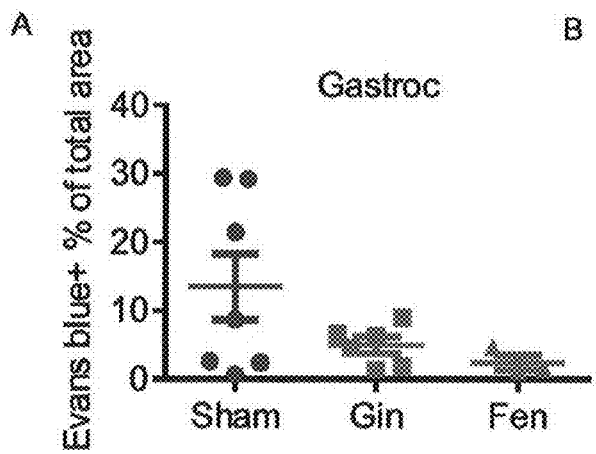
FIGS. 10A-10G are a series of graphs showing the histological and physiological findings of 10-week old mice treated with Ginsenoside Rd (gin) (10 mg/kg) or fenofibrate (fen) (0.1% w/w).
Figure 10B:
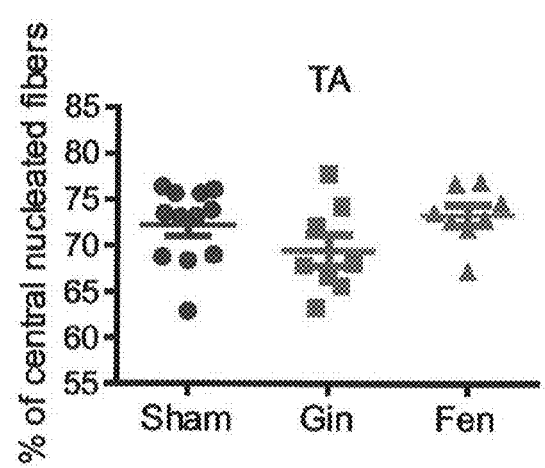
Figure 10C:
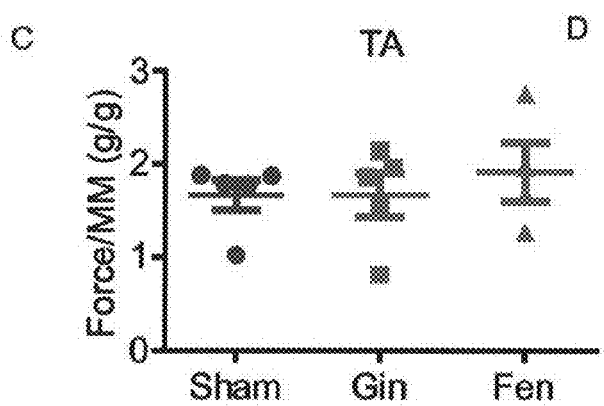
Figure 10D:
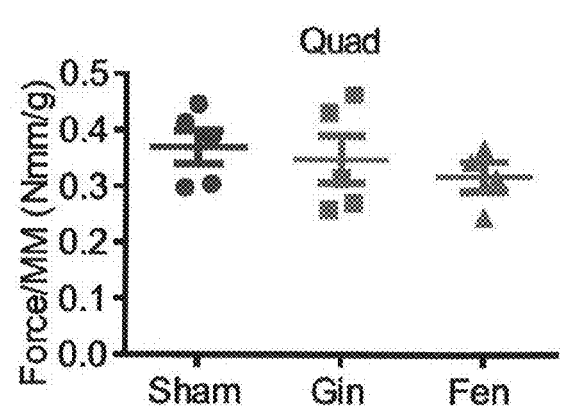
Figure 10E:
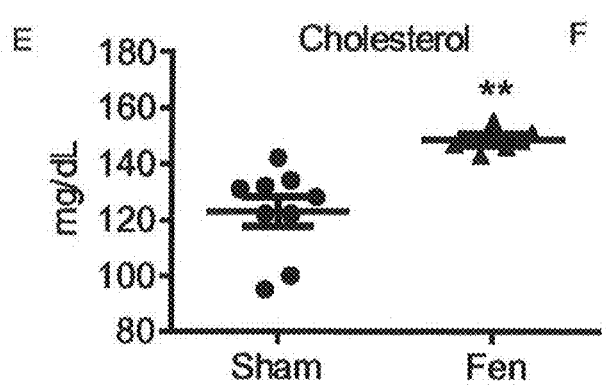
Figure 10F:
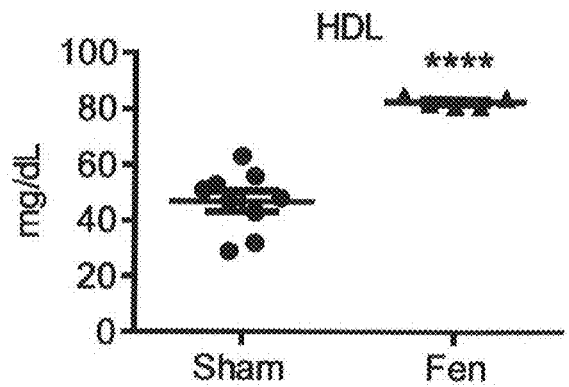
Figure 10G:
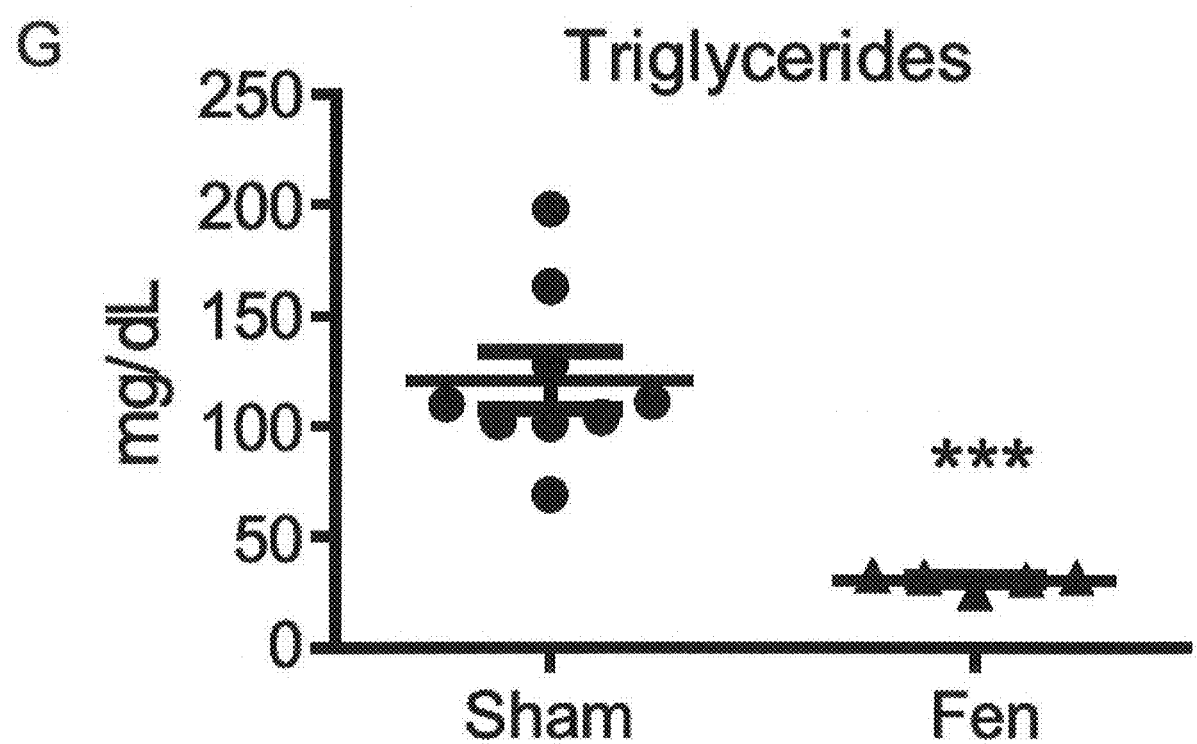

The number of Evans blue dye positive fibers (a marker of cell membrane damage) and central nucleated fibers (a marker of muscle degeneration and regeneration) were not significantly different in treated muscles (FIG. 10A). A series of physiological tests were performed to assess muscle function, including grip strength and treadmill running. Both fenofibrate and ginsenoside Rd improved mdx mouse forelimb grip strength by 16% and 19%, respectively (FIG. 4E). Fenofibrate treatment improved the endurance on treadmill running by 50% compared with control mdx mice, while ginsenoside Rd had no effect on treadmill running (FIG. 4F). Interestingly, there was no significant difference in the maximal isometric force generated by tibialis anterior (TA) or quadriceps muscle with either treatment compared with sham control (FIGS. 10C-10D). However, repeated maximal isometric contractions showed that the TA muscles of treated mice were less susceptible to fatigue compared to mdx TA muscles (FIG. 4G). As expected based on previous studies, mdx quadriceps (Quad) muscles were highly susceptible to injury (78±5.3% loss in muscle force after injury), but treatment with ginsenoside Rd or fenofibrate resulted in significantly less contraction-induced injury (56±4.8% and 50±3.5% loss in muscle force, respectively) (FIG. 4H). Overall, the ginsenoside Rd and fenofibrate treatment significantly ameliorated disease phenotypes in the mdx mice.

Discussion

Drug discovery and repurposing for treating DMD has mostly employed two strategies: restoring dystrophin expression, and modifying downstream pathological pathways, including inflammation, fibrosis, and iPSC for oxidative stress (Blat Y & Blat S (2015) Drug Discovery of Therapies for Duchenne Muscular Dystrophy. *Journal of Biomolecular Screening* 20(10):1189-1203). A rapid and relevant method to identify disease-modifying treatments for DMD could enable a swift translation process, from drug screening to therapy. To improve drug discovery and repurposing of known or approved drugs for DMD, human dystrophic muscle cells that demonstrate the distinguishable DMD phenotype instigated by the lack of dystrophin expression are needed. Recently, the use of human induced pluripotent stem cells (hiPSCs) has gained interest as an emerging approach in drug discovery for genetic diseases. hiPSCs provide a scalable source of starting material that can be easily used in drug screening for DMD. Despite this advantage, there have been no reported applications of hiPSC for drug screens of DMD due to the lack of efficient and reproducible DMD hiPSC models.

During the past 3 years protocols have emerged for myogenic differentiation of DMD hiPSCs. Applying Wnt agonist and Notch antagonist, Choi et al. (*Cell Reports* 15(10):2301-2312; 2016) depicted a distinct transcription profile and phenotype of DMD hiPSC-derived my-oblasts from healthy controls. With Wnt activation and BMP inhibition, Choi et al. reported that myotubes formed from myoblasts derived from mdx mice presented abnormal branching. While both differentiation protocols showed myogenic commitment and ex vivo contraction of skeletal muscle myotubes, Hicks et al. (*Nature cell biology* 20(1): 46-57; 2018) using Choi's protocol did not report a fusion defects in myoblasts derived from DMD hiPSCs following NCAM$^+$/HNK1$^-$ purification. The discrepancy in reported phenotypes of NCAM$^+$/HNK1$^-$ DMD hiPSC-derived myoblasts could be due to that IGF-1 and HGF growth factors which were used in Choi's protocol can enhance the myoblast fusion potential (Sotiropoulos A, et al. (2006) *Proceedings of the National Academy of Sciences of the United States of America* 103(19):7315-7320; Gonzalez M N, et al. (2017) *Skelet. Muscle* 7(1):2039, 40). In comparison, the myoblast culture system described herein, does not contain any growth factors, demonstrating the native myotube formation potential. Moreover, the transcriptional and translational profile data showed increased BMP and TGF-β signaling in DMD hiPSC derived myoblasts. A similar phenomenon was found in myoblasts isolated from DMD patient biopsies and these myoblasts also demonstrated limited growth capability. Using the hiPSC differentiation method described above, an imaging-based screening system was developed herein, where myotube formation was visualized by staining the chemically-induced DMD iPSC-derived myoblasts with antibodies. This straightforward, easily detectable phenotype via imaging can be used in future compound library screens.

The JHCCL used in this study contains around 1000 FDA-approved and 500 foreign-approved compounds. While designing and approving a new drug is very costly and time consuming, screening approved drugs for previously unidentified activities could significantly speed up the process of drug development. Using this compound library together with the imaging-based screen system described above, two final compounds were selected—ginsenoside Rd and fenofibrate. Ginsenosides are a group of active components found in *Panax ginseng*, a well-known herbal medicine touted to improve thinking, concentration, memory, work efficiency, physical stamina, and athletic endurance. Although the therapeutic potential of *ginseng* has been studied extensively, ginsenosides, which belong to the saponin family, have not yet been thoroughly investigated. The reported functions of ginsenosides are mainly composed of anti-inflammatory and anti-oxidant effects. Ginsenoside Rd was chosen among all the ginsenosides because of its function in inhibiting calcium influx (a hallmark of DMD pathology), inhibiting ROS, decreasing cellular apoptosis, and stabilizing the mitochondrial membrane potential. In this study, it was found that ginsenoside Rd helped restore fusion of DMD hiPSC-derived myoblasts. Gene ontology analyses was performed using microarray results from DMD hi-PSC-derived myoblasts treated with ginsenoside Rd to uncover this drug's mechanism. It was found that mitochondria complex II assembly was positively regulated, which might be relevant to the protective function of mitochondria in the presence of ginsenoside Rd. When analyzing the pathways affected by ginsenoside Rd treatment, FLT3 pathway topped the most significantly regulated pathways. FLT3, which is a type III tyrosine kinase, and its mutation in leukemia results in aberrant cell growth. So far, there has been only one study reporting FLEKR phT3 as necessary for myogenic differentiation, where overexpression of FLT3 appeared to promote cell cycle exit and activity through p120RasGAP phosphorylation was observed in D2 myoblasts by recombinant FLT3 (100 ng/ml) treatment as well as ginsenoside Rd (20 μM) treatment (FIG. 3D-E). In the leukemia study, activated FLT3 receptor is known to induce RAS/ERK activation. Additionally, several reports have claimed that ERK phosphorylation is induced when myoblasts are terminally differentiated into myotubes. Therefore, in view of that, FLT3 is more likely to activate ERK and induce D2 myoblast differentiation upon recombinant FTL3 or Ginsenoside Rd treatment. In this study, when ginsenoside Rd was given to mdx mice, it improved their forelimb grip strength and increased their resistance to fatigue. This outcome could be the result of ginsenoside Rd's combined effects, including its anti-inflammatory and anti-oxidant function on muscle as well as its effect on promoting myotube differentiation.

The other identified compound, fenofibrate, is a well-established drug to treat hypertriglyceridemia, low HDL-C levels, or dyslipidemia. Fenofibrate's metabolite-fibrate acid—is a PPARα agonist that can reregulate fatty acid metabolism genes to reduce low-density lipoprotein (LDL), total cholesterol and triglycerides and increase high-density lipoprotein (HDL). In this study, when mdx mice were administrated with 0.1% wt/wt fenofibrate diet, they showed decreased triglyceride levels (FIG. 10G) and increased HDL levels (FIG. 10F), similar to what has been reported in humans (Najib J (2002). *Clinical therapeutics* 24(12):2022-2050). There have been reports suggesting fenofibrate is beneficial to muscle function. In one study, fenofibrate was shown to decrease glucocorticoid levels, thereby preventing muscle wasting in small lung cancer patients. Another study showed that fenofibrate administration in arthritic rats inhibited the expression of myostatin in skeletal muscle, prohibiting muscle atrophy. The results here demonstrated that fenofibrate inhibited TGF-β signaling activity (FIGS. 3F-3G). TGF-β signaling has been extensively studied in the context of muscular dystrophy due to its role as a negative regulator of muscle growth and inducer of fibrosis. Decreased fibrosis and increased muscle function was observed in the fenofibrate-treated mdx mice, further supporting the mechanism of fenofibrate as an inhibitor of TGF-β signaling.

In summary, this study shows the application of hiPSC-derived myoblasts in a high-content imaging-based drug screening platform to discover two compounds, ginsenoside Rd and fenofibrate. These two compounds ameliorated the dystrophic phenotype in the mdx mouse model raising the possibility that these drugs could be trialed in DMD. This study presents the feasibility of a set of hiPSC-based medium-scale drug screening to identify FDA-approved drugs or natural products for orphan diseases.

| Target gene | Forward primer | Reverse primer |
|---|---|---|
| SMAD7 | AGCCGACTCTGCGAACTAGA (SEQ ID NO: 4) | ATTCGTTCCCCCTGTTTCA (SEQ ID NO: 5) |
| SKI | ACTGGAAGGCGAGACCATCT (SEQ ID NO: 6) | AGCACCGAGTTGAGAATCTGC (SEQ ID NO: 7) |
| NOS3-2 | GATCCCCCAGAACTCTTCCT (SEQ ID NO: 8) | CAGGGCTGCAAACCACTC (SEQ ID NO: 9) |
| HSP90B1 | CTGGAAATGAGGAACTAACAGTCA (SEQ ID NO: 10) | TCTTCTCTGGTCATTCCTACACC (SEQ ID NO: 11) |
| PRKG1 | TTCTGAATTTGAAAGTCTTCATGC (SEQ ID NO: 12) | CAGCATTTCCTCAACAGTGG (SEQ ID NO: 13) |
| LIPG | GGGAGCCCCGTACCTTTTG (SEQ ID NO: 14) | CCTCACAGATGGTTTGACCTCA (SEQ ID NO: 15) |
| NLRP12 | AGACTGGGGCCTGTGGTT (SEQ ID NO: 16) | TGTGAGGCCACAGCTATCC (SEQ ID NO: 17) |
| U2AF2 | CAGGCCTCACGACTACCAG (SEQ ID NO: 18) | GGGACCACAGTGGACACAA (SEQ ID NO: 19) |
| DNAH5 | TGGATTGCATGTTTGATGCT (SEQ ID NO: 20) | AACCCAGTGTACTAGAAATCCAAGA (SEQ ID NO: 21) |
| RANBP3L | TTCCCAACCATCACGAAAAT (SEQ ID NO: 22) | TTTTGTTGAATATGAAAAGCTTGC (SEQ ID NO: 23) |
| CLEC7A | TGAGATAGGGTCTCACTTTGTTACC (SEQ ID NO: 24) | GCTGAGGCGAGAGATAGCTG (SEQ ID NO: 25) |
| TATDN2 | GGAAGCGCTTAGGCATCTC (SEQ ID NO: 26) | GTTTCCAAGCCCACAACG (SEQ ID NO: 27) |
| ARHGAP42 | CATTTAAATTTGTCCGCAAAGAA (SEQ ID NO: 28) | GAAGTTCTGATGTTCTCGGTCA (SEQ ID NO: 29) |
| MGEA5 | GGAAACAGCGGAAGACCTAAG (SEQ ID NO: 30) | GGTCCTGTCCTCGTTCTCTG (SEQ ID NO: 31) |
| LRRC20 | CCAACTGACAACACCAGTAACTAAA (SEQ ID NO: 32) | TCACAAAGGGCCTGAGC (SEQ ID NO: 33) |
| EGFLAM | CCAGAAGTTTTCAGCCCTCA (SEQ ID NO: 34) | CGTGGAGTTCCGCTTTGA (SEQ ID NO: 35) |
| CLCA2 | GCCAATGTGAAACAGGGATT (SEQ ID NO: 36) | AGGAGTCTCAGCGTAACAGGA (SEQ ID NO: 37) |
| LUZP2 | CACAAAGAAAGTCCCCCAAG (SEQ ID NO: 38) | ACCTCACATTCAGAGCAAGGA (SEQ ID NO: 39) |

-continued

| Target gene | Forward primer | Reverse primer |
|---|---|---|
| GABRB1 | TGGGTGTCTTTTTGGATCAAC (SEQ ID NO: 40) | TGTAAGCACTGTCGTGATTCCT (SEQ ID NO: 41) |
| GMNC | ACGGAGACTTGGGTCTCTTTC (SEQ ID NO: 42) | TCCGGAAGAGGAAAATTTGA (SEQ ID NO: 43) |
| CBL | TGACGTATGACGAAGTGAAAGC (SEQ ID NO: 44) | CAGCTCAGCCGGAAGATATAA (SEQ ID NO: 45) |
| GABRB3 | GAAGGCTTTTCGGCATCTT (SEQ ID NO: 46) | CCGGGATCGTTCACACTC (SEQ ID NO: 47) |
| WNT2 | TTTGGCAGGGTCCTACTCC (SEQ ID NO: 48) | CCTGGTGATGGCAAATACAA (SEQ ID NO: 49) |
| SDHAF3 | AAGACCGTTGGTTCTGACGAGG (SEQ ID NO: 50) | TCTTCTGGGAGGAAGGTGCCAA (SEQ ID NO: 51) |
| ESR1 | GCTTACTGACCAACCTGGCAGA (SEQ ID NO: 52) | GGATCTCTAGCCAGGCACATTC (SEQ ID NO: 53) |
| RPL12 | GTGCACCGGAGGTGAAGT (SEQ ID NO: 54) | TGGCAATGTCATCACCAACT (SEQ ID NO: 55) |
| DGCR8 | TGCAAAGATGAATCCGTTGA (SEQ ID NO: 56) | AGTAACTTGCTCAAAGTCAAAACG (SEQ ID NO: 57) |
| PIP5K1C | ACACAGTCGTCTGGACAGGA (SEQ ID NO: 58) | CCACCTGCACTGTAATCTGC (SEQ ID NO: 59) |
| DNAJC11 | AAATGCACATATCCCAGTCCA (SEQ ID NO: 60) | GGTTGAGAGGCTTCCAGAGAG (SEQ ID NO: 61) |
| ANKRD36C | GGAGAGCAAAAGAGGCTTGA (SEQ ID NO: 62) | GCTCACAGTGATTATCTTTAAGTTCTG (SEQ ID NO: 63) |
| SPAG5 | TTTGCTCAGCGTCACACAG (SEQ ID NO: 64) | TCGGTTTCCTCTAAGTCCATTC (SEQ ID NO: 65) |
| OR51T1 | AGCGGAGACTCCACAAACC (SEQ ID NO: 66) | AATGGTCAGACATAGATCAACAGC (SEQ ID NO: 67) |
| TATDN2 | GGAAGCGCTTAGGCATCTC (SEQ ID NO: 68) | GTTTCCAAGCCCACAACG (SEQ ID NO: 69) |
| GPC4 | GGAGATGTCGTGAGCAAGGT (SEQ ID NO: 70) | CTTCAACAGGGCATGGGTA (SEQ ID NO: 71) |
| FCHO1 | TTGTACACACAACCGCTATTGA (SEQ ID NO: 72) | CACTCTGGGAGGGGTCACT (SEQ ID NO: 73) |
| BPGM | CTAGGAGGCGCTGGCTCT (SEQ ID NO: 74) | TCAAATGGGCTAATATTCAAGGA (SEQ ID NO: 75) |
| ITIH4 | CAGCACGTCCTGGAGTCA (SEQ ID NO: 76) | CGAAGGGAGTGTCTCACTCAT (SEQ ID NO: 77) |
| BBX | CACCTCTCTGCGAGCTAATGT (SEQ ID NO: 78) | TCTTCATTCCAACACCCTTCA (SEQ ID NO: 79) |
| ERV3 | GACCCACTGGAAGCCTAGAA (SEQ ID NO: 80) | CTAGGTCCTGTTGGCTGGTC (SEQ ID NO: 81) |
| SRP54 | TGCAGGGAGCATACAGAAAG (SEQ ID NO: 82) | ATGCACCAAGGTGAACTGTG (SEQ ID NO: 83) |
| CDKL5 | TCCATCGAGATATAAAACCAGAAA (SEQ ID NO: 84) | CCTTCTGACAGATTACGAGCAA (SEQ ID NO: 85) |

Other Embodiments

From the foregoing description, it will be apparent that variations and modifications may be made to the invention described herein to adopt it to various usages and conditions. Such embodiments are also within the scope of the following claims.

All citations to sequences, patents and publications in this specification are herein incorporated by reference to the same extent as if each independent patent and publication was specifically and individually indicated to be incorporated by reference.

What is claimed is:

1. A method of screening for candidate therapeutic agents, comprising: obtaining fibroblasts from a subject diagnosed as having a muscular dystrophy and generating induced pluripotent stem cells (iPSCs); culturing the iPSCs; differentiating the iPSCs to generate myoblasts; contacting the myoblasts with a candidate therapeutic agent; culturing the myoblasts with a detectably labeled anti-myosin heavy chain antibody; and, imaging and analyzing the myoblasts generated from the iPSCs of the subject diagnosed with muscular dystrophy as compared to myoblasts generated from a healthy subject's iPSCs, wherein the analysis comprises measuring average length of myoblasts and expression of myosin heavy chain (MyHC) polypeptides as compared to positive and negative controls; and wherein the average length of myoblasts is determined by: cell average length+ 0.3*MyHC (myosin heavy chain); thereby, screening for the candidate therapeutic agent.

2. The method of claim 1, wherein the detectable label comprises an anti-myosin antibody detected by: an immunofluorescent agent, radio labeled molecules fluorophores, radiochemical, luminescent compounds, electron-dense reagents, enzymes, biotin, radioactive compounds, non-radioactive compounds or digoxigenin.

3. The method of claim 2, wherein the detectable label is an immunofluorescent agent.

4. The method of claim 1, wherein the expression of myosin heavy chain is detected by intensity of immunofluorescent staining of MyHC polypeptides.

5. The method of claim 1, wherein the candidate therapeutic agents have an equal or higher value than an average value of a positive control as measured by myoblast average length+0.3*MyHC and intensity of MyHC staining.

6. The method of claim 1, wherein a candidate therapeutic agent enhances myogenic fusion abilities of myoblasts from the subject diagnosed as having a muscular dystrophy as compared to a control.

7. The method of claim 1, further comprising measuring dose responses to a candidate therapeutic agent as determined by anti-MyHC immunocytochemistry, anti-α-actinin immunocytochemistry and average myoblast length.

8. The method of claim 1, wherein the iPSCs are cultured as single cells on defined extracellular matrix material in serum-free media.

9. The method of claim 1, wherein the iPSCs are cultured in medium comprising a Wnt agonist and Notch antagonist to generate myoblasts.

10. The method of claim 9, further comprising identifying the myoblasts by an expression profile as neural cell adhesion molecule positive and human natural killer-1 negative (NCAM$^+$/HNK1$^-$).

11. The method of claim 1, wherein the muscular dystrophy is Duchenne muscular dystrophy (DMD), Becker muscular dystrophy, congenital muscular dystrophy, myotonic dystrophy, facioscapulohumeral muscular dystrophy (FSHD), limb-girdle muscular dystrophy, oculopharyngeal muscular dystrophy, distal muscular dystrophy or Emery Dreifuss muscular dystrophy.

12. The method of claim 11, wherein the muscular dystrophy is Duchenne muscular dystrophy (DMD).

13. A method of screening for candidate therapeutic agents, comprising:
   obtaining fibroblasts from a subject diagnosed as having a muscular dystrophy and generating induced pluripotent stem cells (iPSCs);
   culturing the iPSCs;
   differentiating the iPSCs to generate myoblasts;
   contacting the myoblasts with a candidate therapeutic agent;
   culturing the myoblasts with a detectably labeled anti-myosin heavy chain antibody; and,
   imaging and analyzing the myoblasts generated from the iPSCs of the subject diagnosed with muscular dystrophy as compared to myoblasts generated from a healthy subject's iPSCs, wherein the analysis comprises measuring average length of myoblasts and expression of myosin heavy chain (MyHC) polypeptides as compared to positive and negative controls; wherein the candidate therapeutic agents have an equal or higher value than an average value of a positive control as measured by myoblast average length+0.3*MyHC and intensity of MyHC staining; thereby, screening for the candidate therapeutic agent.

* * * * *

SEQUENCE LISTING

```
<160> NUMBER OF SEQ ID NOS: 89

<210> SEQ ID NO 1
<211> LENGTH: 60
<212> TYPE: DNA
<213> ORGANISM: Homo sapiens

<400> SEQUENCE: 1
gtcaaaaatg taatgaaaaa tatcatggct ggattgcaac aaaccaacag tgaaaagatt      60

<210> SEQ ID NO 2
<211> LENGTH: 60
<212> TYPE: DNA
<213> ORGANISM: Homo sapiens

<400> SEQUENCE: 2
ctcctgagct gggtccgaca atcaactcgt aattatccac aggttaatgt aatcaacttc      60

<210> SEQ ID NO 3
<211> LENGTH: 53
<212> TYPE: DNA
<213> ORGANISM: Homo sapiens

<400> SEQUENCE: 3
accaccagct ggtctgatgg cctggctttg aatgctctca tccatagtca tag             53

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccgactct gcgaactaga                                                  20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
attcgttccc cctgtttca                                                   19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actggaaggc gagaccatct                                                  20
```

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcaccgagt tgagaatctg c                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatcccccag aactcttcct                                                20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagggctgca aaccactc                                                  18

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggaaatga ggaactaaca gtca                                           24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcttctctgg tcattcctac acc                                            23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttctgaattt gaaagtcttc atgc                                           24
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagcatttcc tcaacagtgg                                              20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggagccccg tacctttg                                                19

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctcacagat ggtttgacct ca                                           22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agactggggc ctgtggtt                                                18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtgaggcca cagctatcc                                               19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caggcctcac gactaccag                                               19

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggaccacag tggacacaa                                                   19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggattgcat gtttgatgct                                                  20

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aacccagtgt actagaaatc caaga                                            25

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttcccaacca tcacgaaaat                                                  20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttttgttgaa tatgaaaagc ttgc                                             24

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgagataggg tctcactttg ttacc                                            25

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctgaggcga gagatagctg                                              20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggaagcgctt aggcatctc                                               19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtttccaagc ccacaacg                                                18

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
catttaaatt tgtccgcaaa gaa                                          23

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaagttctga tgttctcggt ca                                           22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggaaacagcg gaagacctaa g                                            21

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggtcctgtcc tcgttctctg                                             20

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccaactgaca acaccagtaa ctaaa                                       25

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcacaaaagg gcctgagc                                               18

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccagaagttt tcagccctca                                             20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgtggagttc cgctttga                                               18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gccaatgtga aacagggatt                                             20

<210> SEQ ID NO 37
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
aggagtctca gcgtaacagg a                                              21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacaaagaaa gtcccccaag                                                20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acctcacatt cagagcaagg a                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tgggtgtctt tttggatcaa c                                              21

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtaagcact gtcgtgattc ct                                             22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acggagactt gggtctcttt c                                              21

<210> SEQ ID NO 43
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
tccggaagag gaaaatttga                                                    20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgacgtatga cgaagtgaaa gc                                                 22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cagctcagcc ggaagatata a                                                  21

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaaggctttt cggcatctt                                                     19

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccgggatcgt tcacactc                                                      18

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tttggcaggg tcctactcc                                                     19

<210> SEQ ID NO 49
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 49
cctggtgatg gcaaatacaa                                                    20

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aagaccgttg gttctgacga gg                                                 22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcttctggga ggaaggtgcc aa                                                 22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gcttactgac caacctggca ga                                                 22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggatctctag ccaggcacat tc                                                 22

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtgcaccgga ggtgaagt                                                      18

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
tggcaatgtc atcaccaact                                           20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgcaaagatg aatccgttga                                           20

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agtaacttgc tcaaagtcaa aacg                                      24

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acacagtcgt ctggacagga                                           20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccacctgcac tgtaatctgc                                           20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaatgcacat atcccagtcc a                                         21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggttgagagg cttccagaga g                                          21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggagagcaaa agaggcttga                                            20

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gctcacagtg attatcttta agttctg                                    27

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tttgctcagc gtcacacag                                             19

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tcggtttcct ctaagtccat tc                                         22

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
agcggagact ccacaaacc                                             19

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 67
aatggtcaga catagatcaa cagc                                          24

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggaagcgctt aggcatctc                                                19

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtttccaagc ccacaacg                                                 18

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggagatgtcg tgagcaaggt                                               20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cttcaacagg gcatgggta                                                19

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ttgtacacac aaccgctatt ga                                            22

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```
cactctggga ggggtcact                                                19

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctaggaggcg ctggctct                                                 18

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcaaatgggc taatattcaa gga                                           23

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cagcacgtcc tggagtca                                                 18

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgaagggagt gtctcactca t                                             21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cacctctctg cgagctaatg t                                             21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
tcttcattcc aacacccttc a                                              21
```

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
gacccactgg aagcctagaa                                                20
```

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
ctaggtcctg ttggctggtc                                                20
```

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

```
tgcagggagc atacagaaag                                                20
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

```
atgcaccaag gtgaactgtg                                                20
```

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

```
tccatcgaga tataaaacca gaaa                                           24
```

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85

```
ccttctgaca gattacgagc aa                                             22
```

```
<210> SEQ ID NO 86
<211> LENGTH: 13
<212> TYPE: DNA
<213> ORGANISM: Homo sapiens

<400> SEQUENCE: 86
ttatccacag gtt                                                          13

<210> SEQ ID NO 87
<211> LENGTH: 13
<212> TYPE: DNA
<213> ORGANISM: Homo sapiens

<400> SEQUENCE: 87
ttatccatag gtt                                                          13

<210> SEQ ID NO 88
<211> LENGTH: 173
<212> TYPE: DNA
<213> ORGANISM: Homo sapiens

<400> SEQUENCE: 88
gtcaaaaatg taatgaaaaa tatcatggct ggattgcaac aaaccaacag tgaaaagatt       60
ctcctgagct gggtccgaca atcaactcgt aattatccac aggttaatgt aatcaacttc      120
accaccagct ggtctgatgg cctggctttg aatgctctca tccatagtca tag             173

<210> SEQ ID NO 89
<211> LENGTH: 173
<212> TYPE: DNA
<213> ORGANISM: Homo sapiens

<400> SEQUENCE: 89
gtcaaaaatg taatgaaaaa tatcatggct ggattgcaac aaaccaacag tgaaaagatt       60
ctcctgagct gggtccgaca atcaactcgt aattatccat aggttaatgt aatcaacttc      120
accaccagct ggtctgatgg cctggctttg aatgctctca tccatagtca tag             173
```